US008676329B2

(12) United States Patent
Wacnik et al.

(10) Patent No.: US 8,676,329 B2
(45) Date of Patent: Mar. 18, 2014

(54) DORSAL COLUMN STIMULATION THERAPY

(75) Inventors: Paul W. Wacnik, Pittsburgh, PA (US); Lisa M. Johanek, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 428 days.

(21) Appl. No.: 12/855,459

(22) Filed: Aug. 12, 2010

(65) Prior Publication Data
US 2011/0040348 A1   Feb. 17, 2011

Related U.S. Application Data

(60) Provisional application No. 61/233,457, filed on Aug. 12, 2009, provisional application No. 61/233,479, filed on Aug. 12, 2009.

(51) Int. Cl.
*A61N 1/05* (2006.01)
(52) U.S. Cl.
USPC .......................................................... 607/46
(58) Field of Classification Search
USPC .......................................................... 607/46
See application file for complete search history.

(56) References Cited

U.S. PATENT DOCUMENTS

| | | | |
|---|---|---|---|
| 5,143,081 A | 9/1992 | Young et al. | |
| 5,792,212 A | 8/1998 | Weijand | |
| 5,871,099 A * | 2/1999 | Mellenthin et al. | 206/781 |
| 6,002,964 A | 12/1999 | Feler et al. | |
| 6,675,046 B2 | 1/2004 | Holsheimer | |
| 6,871,099 B1 | 3/2005 | Whitehurst et al. | |
| 7,483,747 B2 | 1/2009 | Gliner et al. | |
| 7,502,651 B2 | 3/2009 | Kim et al. | |
| 2006/0167525 A1 | 7/2006 | King | |
| 2006/0241721 A1 | 10/2006 | Kothandaraman et al. | |
| 2006/0259099 A1 | 11/2006 | Goetz et al. | |
| 2007/0073357 A1 | 3/2007 | Rooney et al. | |
| 2007/0179579 A1 | 8/2007 | Feler et al. | |
| 2008/0300655 A1 | 12/2008 | Cholette | |
| 2011/0054565 A1 | 3/2011 | Wacnik et al. | |

FOREIGN PATENT DOCUMENTS

WO   2008121891 A1   10/2008
WO   2009055207 A2   4/2009

OTHER PUBLICATIONS

International Search Report and Written Opinion for corresponding PCT Application No. PCT/US2010/045351 dated Dec. 3, 2010 (10 pgs.).
Haque et al., "Transforaminal Nerve Root Stimulation: A Technical Report," Neuromodulation: Technology at the Neural Interface, vol. 12, No. 3, Feb. 2009 (4 pgs.).
Weigel et al., "Failure of long-term nerve root stimulation to improve neuropathic pain," J. Neurosurg, vol. 108, pp. 921-925, May 2008.

(Continued)

*Primary Examiner* — George Manuel
(74) *Attorney, Agent, or Firm* — Shumaker & Sieffert, P.A.

(57) ABSTRACT

In some examples, the disclosure relates to system, devices, and techniques for delivering dorsal column stimulation. One or more locations for dorsal column stimulation may be identified based on sensed signals evoked by delivery of stimulation to a dorsal root and/or peripheral nerve of a patient. In some examples, an IMD may deliver dorsal column stimulation in combination with dorsal root stimulation to a patient to treat a patient condition.

26 Claims, 11 Drawing Sheets

(56) References Cited

OTHER PUBLICATIONS

Beall et al., "Spinal cord potentials evoked by cutaneous afferents in the monkey," J Neurophysiol, vol. 40 pp. 199-211, (1977).

Jeanmonod et al., "Intra-operative spinal cord evoked potentials during cervical and lumbo-sacral microsurgical DREZ-tomy (MDT) for chronic pain and spasticity (preliminary data)," Acta Neurochir Suppl (Wien ), vol. 46, pp. 58-61 (1989).

Jeanmonod et al., "Three transverse dipolar generators in the human cervical and lumbo-sacral dorsal horn: evidence from direct intraoperative recordings on the spinal cord surface," Electroencephalogr Clin Neurophysiol, vol. 74, pp. 236-240 (1989).

Jeanmonod et al, "The human cervical and lumbo-sacral evoked electrospinogram. Data from intra-operative spinal cord surface recordings," Electroencephalogr Clin Neurophysiol, vol. 80, pp. 477-489 (1991).

Sindou et al., "Intraoperative monitoring of spinal cord SEPs during microsurgical DREZotomy (MDT) for pain, spasticity and hyperactive bladder." Stereotact Funct Neurosurg. vol. 62 pp. 164-170 (1994).

Sindou et al., "Predictive value of somatosensory evoked potentials for long-lasting pain relief after spinal cord stimulation: practical use for patient selection," Neurosurgery, vol. 52, pp. 1374-1383 (2003).

Stanton-Hicks M., "Complex regional pain syndrome: manifestations and the role of neurostimulation in its management,". J Pain Symptom Manage, vol. 31 (4 Suppl.), pp. S20-4 (2006).

Van Buyten JP., "Neurostimulation for chronic neuropathic back pain in failed back surgery syndrome," J Pain Symptom Manage, vol. 31 (4 Suppl.), pp. S25-9 (2006).

Buchser et al., "Spinal cord stimulation for the management of refractory angina pectoris," J Pain Symptom Manage, vol. 31 (4 Suppl.), pp. S36-42 (2006).

Monhemius et al., "Efficacy of spinal cord stimulation for neuropathic pain: assessment by abstinence," Eur J Pain, vol. 7, No. 6, pp. 513-519 (2006).

Hague et al., "Spinal nerve root stimulation," Neurosurg. Focus, vol. 21, vol. 6, Dec. 2006 (7 pgs.).

Office Action dated Feb. 7, 2012 for U.S. Appl. No. 12/855,439 (13 pgs.).

Responsive Amendment dated May 7, 2012 for U.S. Appl. No. 12/855,439 (11 pgs.).

U.S. Appl. No. 12/855,439, filed Aug. 12, 2010 entitled "Dorsal Column Stimulation Therapy,".

Request for Continued Examination (RCE) and Responsive Amendment dated Aug. 16, 2012 for U.S. Appl. No. 12/855,439, (13 pgs.).

Final Office Action dated May 17, 2012 for U.S. Appl. No. 12/855,439, (8 pgs.).

\* cited by examiner

DORSAL COLUMN STIMULATION THERAPY

This application claims the benefit of U.S. Provisional Application Ser. Nos. 61/233,457 and 61/233,479 to Wacnik et al., filed Aug. 12, 2009, and entitled "DORSAL COLUMN STIMULATION THERAPY," the entire content of each of which is incorporated herein by reference.

TECHNICAL FIELD

The disclosure relates to medical devices and, more particularly, to programmable medical devices that deliver electrical stimulation therapy to a patient.

BACKGROUND

A variety of therapies, such as neurostimulation or therapeutic agents, e.g., drugs, may be delivered to a patient to treat chronic or episodic pain. Neurostimulation is typically delivered by an implantable medical device (IMD). An IMD delivers neurostimulation therapy via electrodes, which are coupled to the IMD by one or more leads, or carried by the IMD housing in the case of a leadless stimulator. The number and positions of the leads and electrodes is largely dependent on the type or cause of the pain, and the type of neurostimulation delivered to treat the pain. In general, an IMD delivers neurostimulation therapy in the form of electrical stimulation signals such as pulses.

SUMMARY

In general, the disclosure is directed to systems, devices and techniques for delivering therapy, such as, e.g., electrical stimulation therapy, to a patient. In some examples, the therapy may be delivered to target one or more of a dorsal column, dorsal root, and/or peripheral nerve locations of the patient. In some examples, the therapy delivered to the patient may treat or manage pain experienced by the patient.

In some aspects, the disclosure relates to techniques for selecting or identifying one or more stimulation locations on the dorsal column of a patient, e.g., target stimulation locations on the left and/or right dorsal columns for delivery of stimulation therapy to treat pain experienced by a patient. To select or identify the one or more dorsal column locations, the one or more locations may be evaluated based on one or more parameters of evoked signals sensed at respective dorsal column locations. The evoked signals may be evoked by delivery of stimulation to one or more dorsal root locations and/or one or more peripheral nerve locations. In some examples, the dorsal root and/or peripheral nerve location(s) may be associated with a particular type or location of pain to be treated by the dorsal column stimulation. In some examples, the dorsal column location at which the sensed evoked signal exhibited the largest signal amplitude may be selected for delivery of dorsal column stimulation.

In some aspects, the disclosure relates to delivery of stimulation to one or more locations on the dorsal column of a patient in combination with the delivery of electrical stimulation to one or more dorsal root locations. For example, the dorsal root stimulation may be delivered substantially simultaneously with the dorsal columns stimulation. In other examples, the respective therapies may be delivered in an interleaved manner. In some examples, the dorsal root stimulation may be delivered with one or more therapy parameter values, e.g., stimulation pulse frequency, independent from that of the dorsal column stimulation.

In one example, the disclosure relates to a method comprising delivering electrical stimulation to at least one of a peripheral nerve and a dorsal root of a patient; and sensing a signal evoked by the electrical stimulation at one or more locations on a dorsal column of the patient.

In another example, the disclosure relates to a system comprising a therapy module configured to deliver electrical stimulation to at least one of a peripheral nerve and dorsal root of a patient; and a sensing module configured to sense a signal evoked by the electrical stimulation at one or more locations on a dorsal column of the patient.

In another example, the disclosure relates to a system comprising means for delivering electrical stimulation to at least one of a peripheral nerve and dorsal root of a patient; and means for sensing a signal evoked by the electrical stimulation at one or more locations on a dorsal column of the patient.

In another example, the disclosure relates to a non-transitory computer-readable storage medium comprising instructions that cause a processor to control a therapy module to deliver electrical stimulation to at least one of a peripheral nerve and a dorsal root of a patient; and sense a signal evoked by the electrical stimulation at one or more locations on a dorsal column of the patient.

In another example, the disclosure relates to a method comprising delivering a first stimulation therapy to a dorsal root of a patient; and delivering a second stimulation therapy to a dorsal column of the patient in combination with the delivery of the first stimulation therapy.

In another example, the disclosure relates to a system comprising a therapy module configured to deliver a first stimulation therapy to a dorsal root of a patient and a second stimulation therapy to a dorsal column of the patient; and a processor that controls the therapy module to deliver the first and second therapies in combination with one another.

In another example, the disclosure relates to a system comprising means for delivering a first stimulation therapy to a dorsal root of a patient; and means for delivering a second stimulation therapy to a dorsal column of the patient in combination with the delivery of the first stimulation therapy.

In another example, the disclosure relates to a non-transitory computer-readable storage medium comprising instructions that cause a processor to control a therapy module to deliver a first stimulation therapy to a dorsal root of a patient; and control the therapy module to deliver a second stimulation therapy to a dorsal column of the patient in combination with the delivery of the first stimulation therapy.

The details of one or more examples of the invention are set forth in the accompanying drawings and the description below. Other features, objects, and advantages of the invention will be apparent from the description and drawings, and from the claims.

DETAILED DESCRIPTION

Figure 1A:
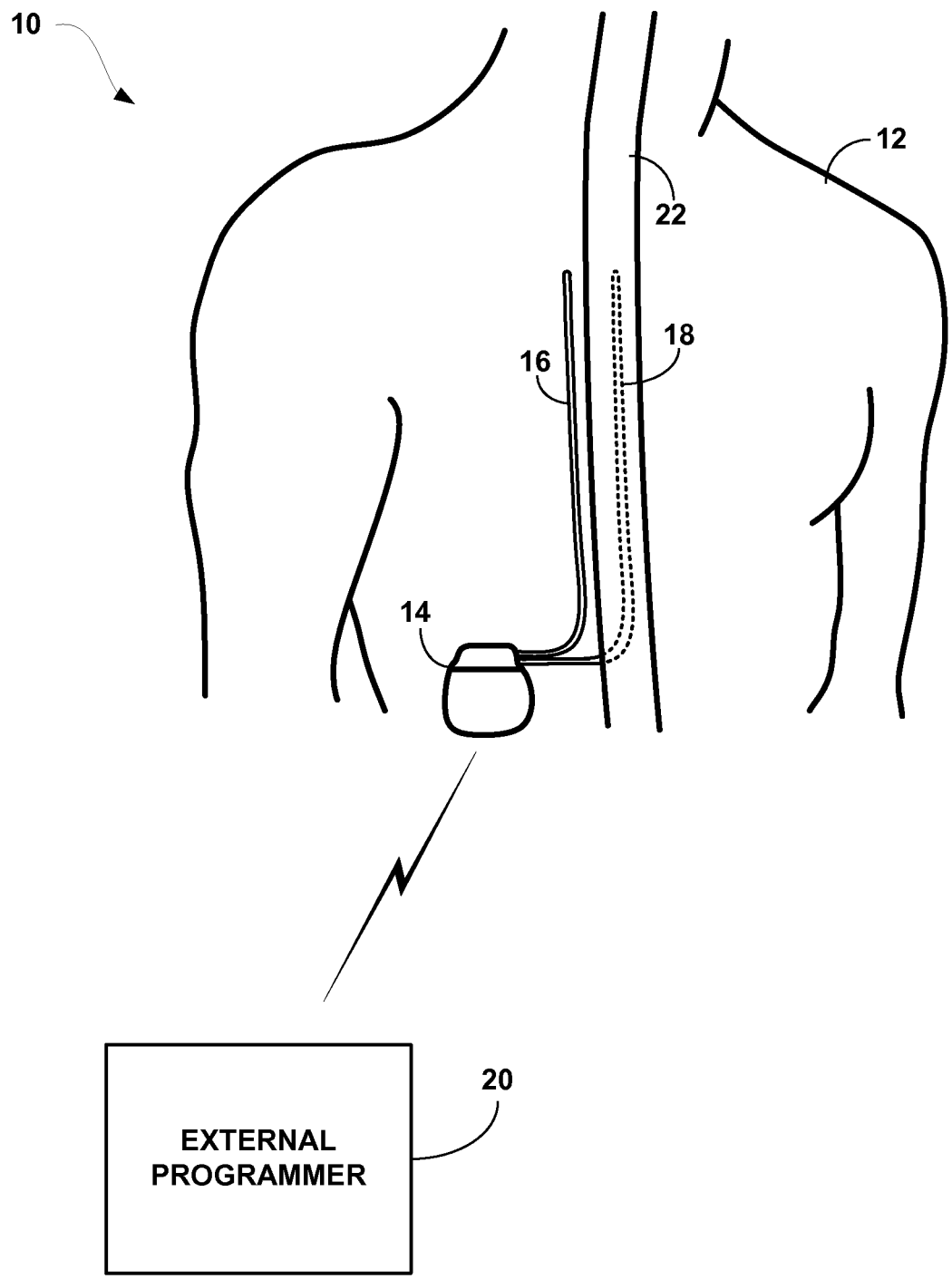
FIG. 1A is a conceptual diagram illustrating an example implantable stimulation system including two implantable stimulation leads.

A medical device, such as an IMD, may deliver electrical stimulation therapy to a patient for a variety of reasons. For example, an IMD may deliver electrical stimulation therapy to treat patients that suffer from chronic back pain, leg pain, or other pain that cannot be effectively or efficiently treated through other methods. Generally, values for one or more stimulation parameters associated with the electrical stimulation therapy can be defined to treat one or more of the conditions experienced by a patient.

The therapeutic efficacy of the stimulation therapy may depend on the particular physiological location at which the electrical stimulation is delivered to the patient. In some examples, an IMD may deliver electrical stimulation therapy to a dorsal root or peripheral nerve associated with a source of pain experienced by a patient in a manner that effectively treats the pain experienced by a patient. It is relatively straight-forward to associate a source of pain with a particular dorsal root or peripheral nerve, as well as identify where on or in the body of a patient to place one or more electrodes to deliver electrical stimulation to a particular dorsal root or peripheral nerve.

In other examples, an IMD may deliver electrical stimulation therapy to one or both of the left and right dorsal columns of a patient to treat a patient condition such as pain. However, unlike peripheral nerve stimulation or dorsal root stimulation, it may be a relatively difficult and often time consuming process to identify one or more particular stimulation locations on the one or both dorsal columns associated with pain experienced by a patient. In some cases, a clinician may use a trial-and-error process to identify a particular location on the dorsal columns for stimulation during which the clinician systematically relocates one or more electrodes to points along the dorsal columns and/or adjusts stimulation electrode combinations. During the process, the clinician may deliver electrical stimulation to a patient at the various locations on one or both of the dorsal columns and evaluate the efficacy of the stimulation delivered to the respective locations based on patient feedback. The patient feedback may include feedback relating to efficacy of the stimulation in providing pain relief, as well as possible side effects which could undermine efficacy. In some cases, a patient may be partially sedated during this process, which may influence the reliability of the feedback elicited from the patient.

Once a target location on the dorsal columns is identified, stimulation may be delivered via one or more electrodes proximate the location in a multipolar or unipolar manner. Multipolar stimulation generally involves delivery of stimulation via two or more electrodes on a lead, whereas unipolar stimulation generally involves delivery of stimulation via one or more electrodes on a lead and one or more electrodes on the IMD housing (which in some examples may be referred to as the IMD can or case). In some cases, target locations on both dorsal columns may be stimulated via leads deployed adjacent the left and right dorsal columns.

Even after a particular location on the dorsal columns has been identified and one or more electrodes have been positioned to deliver electrical stimulation to the location, the therapeutic efficacy of the stimulation may vary over time. For example, lead migration may change the position of the one or more electrodes relative to the dorsal column and, thus, change the location of the dorsal column to which electrical stimulation is delivered. Additionally, even if the position of the one or more electrodes relative to the dorsal columns may stay substantially the same over time, physiological factors may cause the particular location on the dorsal columns for optimal treatment via electrical stimulation to migrate to one or more other locations on the dorsal columns. In each case, the therapeutic efficacy of the electrical stimulation delivered to the dorsal column of the patient may be negatively influenced.

In accordance with some examples of the disclosure, one or more particular stimulation locations on the dorsal columns may be determined by delivering electrical stimulation to a dorsal root and/or peripheral nerve and sensing the signals evoked by the electrical stimulation at one or more locations on the dorsal columns. For example, an IMD may deliver electrical stimulation to a dorsal root and/or peripheral nerve that is associated with the particular condition of a patient to be treated, e.g., a dorsal root and/or peripheral nerve that provides at least a degree of pain relief and/or innervation in response to electrical stimulation. In conjunction with the delivery of electrical stimulation to the peripheral nerve and/or dorsal root, the IMD may monitor one or more locations on the dorsal column via a sensing module to determine the signal evoked at each respective location by the electrical stimulation. Based on one or more parameters of the sensed evoked signal, e.g., signal amplitude, the IMD may identify one or more particular locations for delivery of electrical stimulation to the dorsal column to treat the patient condition. Such a process may be used to position one or more electrodes over the dorsal column of a patient and/or to program stimulation electrode combinations for delivery of stimulation to the dorsal columns of a patient. In some cases, an implanted IMD that delivers chronic therapy to a patient may periodically perform such a process to maintain delivery of stimulation to location(s) on the dorsal columns that provide effective treatment of pain or other patient condition.

In accordance with some examples of the disclosure, electrical stimulation may be delivered to one or more locations on the dorsal columns of a patient in combination with delivery of electrical stimulation to the one or more dorsal roots. For example, an IMD may be configured to deliver dorsal root stimulation to a patient substantially simultaneously with delivery of dorsal column stimulation. In other examples, an IMD may be configured to deliver dorsal root stimulation in combination with delivery of dorsal column stimulation on an interleaved basis. The dorsal column and dorsal root stimulation may be delivered in combination with one another to treat substantially the same patient condition, e.g., to treat the same pain experienced by a patient, while in other examples, the dorsal column and dorsal stimulation may treat different patient conditions, e.g., different pain areas. By delivering dorsal column stimulation and dorsal root stimulation in combination with one another, the effectiveness of the multi-site, coordinated stimulation in treating a patient's pain may be greater than delivering only dorsal column stimulation or only dorsal root stimulation.

FIG. 1 is a schematic diagram illustrating an example implantable stimulation system 10 including a pair of implantable electrode arrays in the form of stimulation leads 16 and 18. Although the techniques described in this disclosure are generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable neurostimulation system for purposes of illustration, but without limitation as to other types of medical devices.

As shown in FIG. 1, system 10 includes an IMD 14 and external programmer 20 shown in conjunction with a patient 12, who is ordinarily a human patient. In the example of FIG. 1, IMD 14 is an implantable electrical stimulator that delivers neurostimulation therapy to patient 12, e.g., for relief of chronic pain or other symptoms. Again, although FIG. 1 shows an IMD, other examples may include an external stimulator, e.g., with percutaneously implanted leads.

Electrical stimulation energy, which may be constant current or constant voltage based pulses, for example, is delivered from IMD 14 to one or more targeted locations within patient 12 via one or more electrodes (not shown) of implantable leads 16 and 18. The parameters for a program that controls delivery of stimulation energy by IMD 14 may include information identifying which electrodes have been selected for delivery of stimulation according to a stimulation program, the polarities of the selected electrodes, i.e., the electrode configuration for the program, and voltage or current amplitude, pulse rate, pulse shape, and pulse width of stimulation delivered by the electrodes. Delivery of stimulation pulses will be described for purposes of illustration. However, stimulation may be delivered in other forms, such as continuous waveforms.

In the example of FIG. 1, leads 16 and 18 may carry one or more electrodes that are placed adjacent to the target tissue. One or more electrodes may be disposed at a distal tip of lead 16 and/or at other positions at intermediate points along lead 16, for example. Electrodes of lead 16 and 18 transfer electrical stimulation generated by an electrical stimulation generator in IMD 14 to tissue of patient 12. The electrodes may be electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 and 118 will be described for purposes of illustration.

Lead 18 may be configured to deliver stimulation energy generated by IMD 14 to one or more targeted locations of the dorsal columns (not shown) of spinal cord 22. For example, one or more electrodes of lead 18 may be implanted adjacent the dorsal columns of spinal cord 22 such that the stimulation field generated by delivery of stimulation energy via the one or more electrodes sufficiently activate one or a group of dorsal column fibers. The delivery of electrical stimulation pulses to one or more locations on the dorsal column may treat pain or other symptoms experienced by patient 12, e.g., by inhibiting pain-like signals. In some cases, delivering stimulation to the appropriate location on the dorsal columns may cause paresthesia that covers the pain region to reduce the area of perceived pain. Dorsal column stimulation can result in the patient experiencing paresthesia in a relatively large area, including more than one limb. In some examples, one or more electrodes of lead 18 may be positioned adjacent to the dorsal columns to deliver stimulation energy to the dorsal columns at approximately the T8, T9, and/or T10 vertebrate levels. The delivery of stimulation to such location(s) may be particularly suitable for treating back pain and/or lower limb pain experienced by a patient. In other examples, one or more electrodes of lead 18 may be positioned adjacent to the dorsal columns to deliver stimulation energy to the dorsal columns in the cervical region. The delivery of stimulation to one or more locations in the cervical region may be particularly suitable for treating upper limb pain experienced by a patient.

Conversely, lead 16 may be configured to deliver stimulation energy generated by IMD 14 to one or more target locations other than the dorsal columns of spinal cord 22. In some examples, lead 16 may be configured to deliver electrical stimulation energy to one or more dorsal roots of spinal cord 22. For example, one or more electrodes on lead 16 may be implanted adjacent one or more dorsal roots, e.g., proximal to the dorsal root entry zone, of spinal cord 22 at one or more vertebrate levels of spinal cord 22. Dorsal roots at particular vertebrate levels may be targeted depending on the area of pain or other patient condition to be treated by the dorsal stimulation. For example, targeting the L2 dorsal root or spinal nerve for stimulation may be appropriate for treating low back dermatome. Similar to stimulation of the dorsal column, dorsal root stimulation may treat pain or other symptoms experienced by patient 12, e.g., by inhibiting pain-like signals. However, the particular type of pain or area of pain treated by dorsal root stimulation may be different than that of the particular type of pain or area of pain treated by dorsal column stimulation.

Additionally or alternatively, lead 16 may be configured to deliver stimulation energy generated by IMD 14 to stimulate one or more peripheral nerves of patient 12, e.g., in the form of peripheral nerve stimulation (PNS). PNS may be used to treat patients suffering from intractable pain secondary to nerve damage isolated to a single nerve. PNS places a group of electrodes in very close proximity to, e.g., in contact with, and approximately parallel to a major nerve in the subcutaneous tissue. PNS may also place a group of electrodes in very close proximity to a nerve that may be deeper in the limb, sometimes near to blood vessels. Placing electrodes in very close proximity to the nerve may ensure that only fibers within that nerve are activated at low amplitudes.

PNS electrodes may be located on percutaneous leads, but for stability and to prevent stimulation of other tissues proximate to the target peripheral nerve, PNS electrodes are generally located within insulative material that wraps around a nerve, i.e., in so-called cuff electrodes, or on one surface of a flat paddle of insulative material placed under a nerve. In any case, the electrodes for PNS are placed in close proximity to the nerve "upstream" from the source of damage or pain, e.g., closer to the spinal cord than the region of damage or pain. When electrodes are implanted upstream, the paresthesia resulting from PNS may extend to a broader area innervated by the target peripheral nerve. The most common upper extremity nerves treated with PNS are the ulnar nerve, median nerve, radial nerve, tibial nerve, occipital nerve, and common peroneal nerve.

As will be described in greater detail below, in some examples, IMD 14 may deliver dorsal root stimulation and/or PNS to patient 12 via lead 16, e.g., to a dorsal root or peripheral nerve that innervates a painful area. In conjunction with the delivery of such stimulation, IMD 14 may monitor one or more locations on the dorsal columns via lead 18 to sense the signals evoked by the dorsal root stimulation and/or PNS. The evoked signal is the electrical signal (or signals) that propagates through a nerve fiber or group of nerve fibers that were activated by the dorsal root stimulation and/or peripheral nerve stimulation. Based on one or more properties of the sensed evoked signal, one or more particular locations on the dorsal column may be identified for delivery of stimulation. For example, the location of the dorsal column associated with the evoked signal that displayed the greatest amplitude (e.g., current amplitude or voltage amplitude) may be identified as the proper target for dorsal column stimulation. The delivery of stimulation to the identified location on the dorsal column may provide effective relief from the pain experienced in the area innervated by the dorsal root and/or peripheral nerve that were stimulated to evoke the sensed signals in the dorsal columns.

Leads 16 and 18 may be implanted within patient 12 directly or indirectly (e.g., via a lead extension) coupled to IMD 14. Alternatively, as mentioned above, leads 16 and 18 may be implanted and coupled to an external stimulator, e.g., through a percutaneous port. In some cases, an external stimulator is a trial or screening stimulation that is used on a temporary basis to evaluate potential efficacy to aid in consideration of chronic implantation for a patient. In additional examples, IMD 14 may be a leadless stimulator with one or more arrays of electrodes arranged on a housing of the stimulator rather than leads that extend from the housing.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 18 is tissue proximate spinal cord 22 and, more particularly, one or more target locations of the dorsal columns. The target tissue for electrical stimulation delivered via lead 16 is tissue adjacent dorsal root or nerve roots that branch off spinal cord 22. Leads 16 and 18 may be introduced into spinal cord 22 via any suitable region, such as the thoracic, cervical or lumbar regions. Stimulation of dorsal columns, dorsal roots, and/or peripheral nerves may, for example, prevent pain signals from traveling through spinal cord 22 and to the brain of the patient. Patient 12 may perceive the interruption of pain signals as a reduction in pain and, therefore, efficacious therapy results.

The deployment of electrodes via leads 16 and 18 is described for purposes of illustration, but arrays of electrodes may be deployed in different ways. For example, a housing associated with a leadless stimulator may carry arrays of electrodes, e.g., rows and/or columns (or other patterns). Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead. In examples in which lead 18 is configured to sense the signals evoked by the delivery of stimulation to a dorsal root and/or peripheral nerve, lead 18 may include an array of electrodes to sense the evoked signal at a plurality of locations on the dorsal columns to provide sensing at a plurality of locations along the dorsal columns.

In the example of FIG. 1, stimulation energy may be delivered by IMD 14 to the dorsal columns, dorsal roots, and/or peripheral nerves to reduce the amount of pain perceived by patient 12. The electrical stimulation delivered by IMD 14 may take the form of electrical stimulation pulses or continuous stimulation waveforms, and may be characterized by controlled voltage levels or controlled current levels, as well as pulse width, pulse rate, pulse burst rate, and/or pulse burst duration in the case of stimulation pulses.

In some examples, IMD 14 generates and delivers stimulation therapy according to one or more programs. A program defines values for one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. Alternatively, multiple programs may contribute to an overall therapeutic effect with respect to a particular type or location of pain. In this manner, IMD 14 may treat different symptoms substantially simultaneously or contribute to relief of the same symptom.

As will be described in greater detail below, in some examples, IMD 14 may deliver dorsal column stimulation via lead 18 in combination with dorsal root stimulation via lead 16. The respective stimulations may be delivered to patient 12 simultaneously or substantially simultaneously with one another or on a time-interleaved basis. In some cases, the respective stimulation may be coordinated with one another based on one or more variables, such as, e.g., type of pain experienced by patient 12, time of day, patient activity, disease progression, patient feedback, and the like. In some cases, the parameters of the respective stimulations, e.g., stimulation programs, may be unique to the stimulation location. For example, IMD 14 may deliver electrical stimulation to one or more locations on the dorsal columns via lead 18 according to a first program while delivering electrical stimulation to one or more dorsal roots locations via lead 16 according to a second program, which may be different from that of the first program.

A user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit particular electrode combinations for dorsal column stimulation to IMD 14 based on evaluation of one or more signal evoked at respective dorsal columns locations by peripheral and/or dorsal root stimulation. As another example, a user may select programs or program groups.

Again, a program may be characterized by an electrode combination, electrode polarities, voltage or current amplitude, pulse width, pulse rate, pulse shape, and/or duration. A group may be characterized by multiple programs that are delivered simultaneously or on an interleaved or rotating basis.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

IMD 14 may be constructed with a biocompatible housing, such as titanium or stainless steel, or a polymeric material such as silicone or polyurethane, and surgically implanted at a site in patient 18 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 and 18 may be tunneled from IMD 14 through tissue to reach the target tissue adjacent to spinal cord 22 for stimulation delivery.

Figure 5:
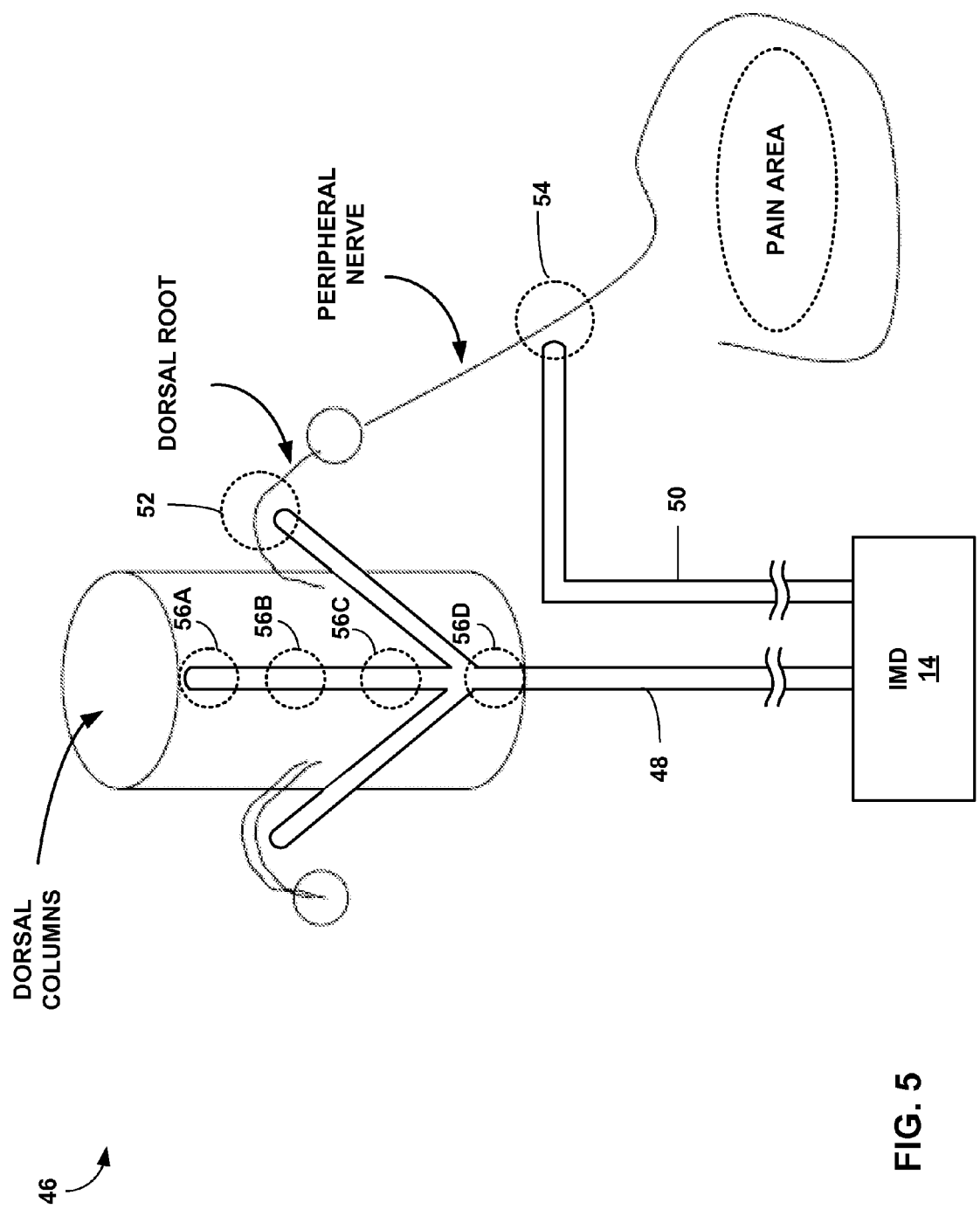
FIG. 5 is a conceptual diagram illustrating an example implantable stimulation system configured to deliver stimulation therapy to a patient.

Implantable stimulation system 10 is not limited to that of two leads, but instead may include zero, one, three, four, five or more than five leads. For example, system 10 may include a third lead in addition to lead 16 and 18. In such a configuration, IMD 14 may deliver stimulation via combinations of electrodes carried by all three leads, or a subset of the three leads. The electrode configuration may be multipolar (e.g., bipolar) or unipolar arrangements. The third lead may include a greater number of electrodes than leads 16 and 18 and be positioned between leads 16 and 18 or on one side of either lead 16 or lead 18. In some examples, the third lead may be positioned proximate to one or more peripheral nerves to deliver PNS while leads 16 and 18 are positioned to deliver dorsal root and dorsal column stimulation, respectively. The number and configuration of all three leads may be stored within external programmer 20 to allow programmer 20 to appropriately program stimulation therapy or assist in the programming of stimulation therapy. In other example, a single lead may be configured to deliver two or more of PNS, dorsal columns stimulation, and dorsal root stimulation. For example, FIG. 5 illustrates an example in which lead 48 is configured to deliver both dorsal root stimulation and dorsal column stimulation from IMD 14.

In some examples, leads 16 and 18 each include four electrodes, while a third lead (not shown) includes eight or sixteen electrodes, thereby forming a so-called 4-8-4 or 4-16-4 lead configuration. Other lead configurations, such as 8-16-8, 8-4-8, 16-8-16, 16-4-16, are possible, whereby the number in the configuration indication refers to the number of electrodes in a particular electrode column, which may be defined by a lead 16, lead 18, and the third lead (not shown). In some cases, electrodes on the third lead may be smaller in size and/or closer together than the electrodes of leads 16 and 18.

Figure 1B:
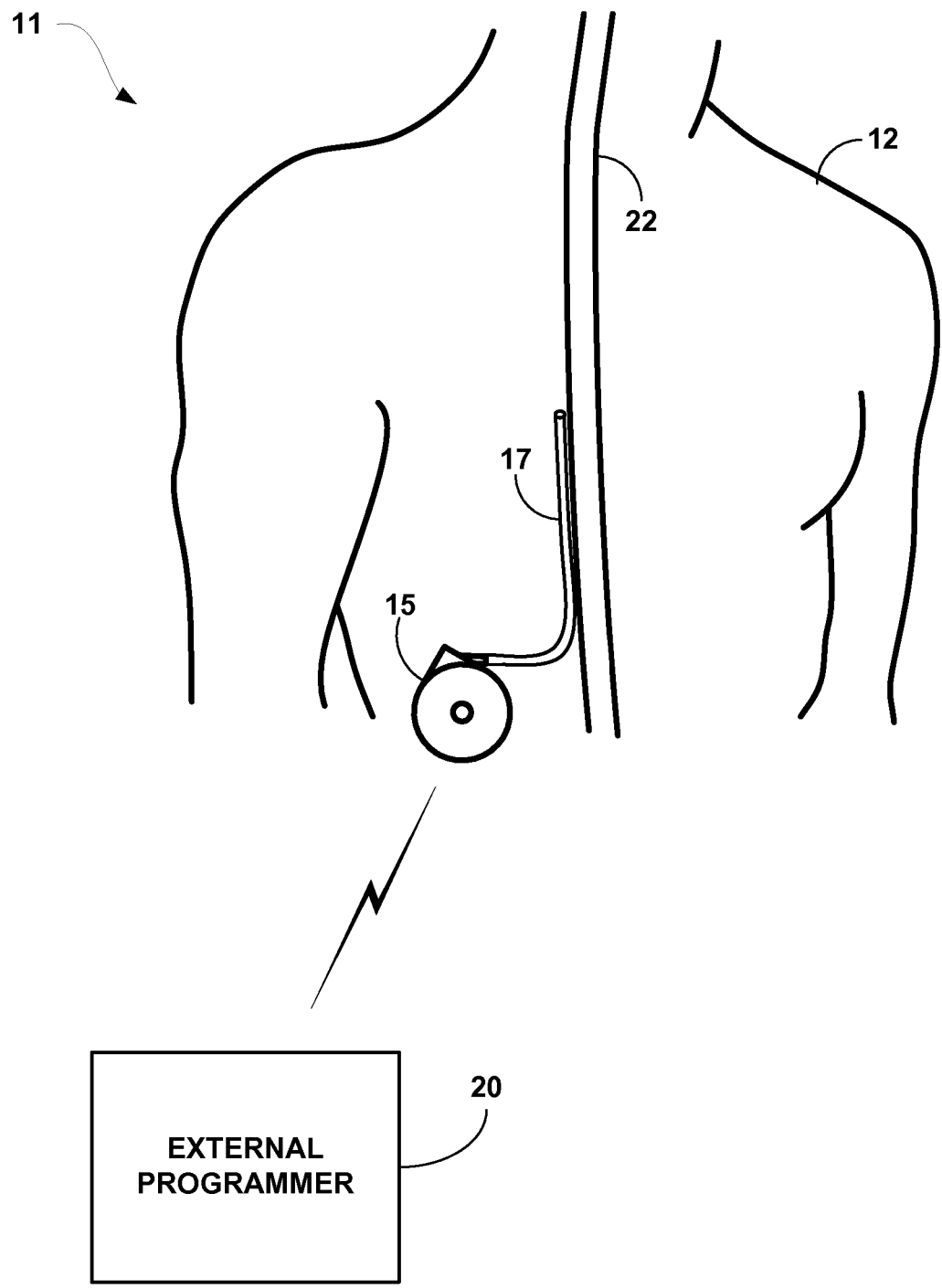
FIG. 1B is a conceptual diagram illustrating an example implantable drug delivery system.

FIG. 1B is a conceptual diagram illustrating an implantable drug delivery system 11 including one delivery catheter 17 coupled to IMD 15. As shown in the example of FIG. 1B, drug delivery system 11 is substantially similar to system 10. However, drug delivery system 11 performs the similar therapy functions via delivery of one or more therapeutic agents instead of electrical stimulation therapy. IMD 15 functions as a drug pump in the example of FIG. 1B, and IMD 15 communicates with external programmer 20 to initialize therapy or modify therapy during operation. In addition, IMD 15 may be refillable to allow chronic drug delivery.

A fluid delivery port of catheter 17 may be positioned within an intrathecal space or epidural space of spinal cord 22. In some examples, a fluid delivery port of catheter 17 may be positioned adjacent to dorsal columns of spinal cord 22 or dorsal roots that branch off of the dorsal columns. Although IMD 15 is shown as coupled to only one catheter 17 positioned along spinal cord 22, additional catheters may also be coupled to IMD 15. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 15 may be an external device that includes a percutaneous catheter to deliver a therapeutic agent to patient 12, e.g., in the same manner as catheter 17. Alternatively, the percutaneous catheter can be coupled to catheter 17, e.g., via a fluid coupler. In other examples, IMD 15 may include both electrical stimulation capabilities as described in IMD 14 (FIG. 1A) and drug delivery therapy.

IMD 17 may also operate using parameters that define the method of drug delivery. IMD 17 may include programs, or groups of programs, that define different delivery methods for patient 12. For example, a program that controls delivery of a drug or other therapeutic agent may include a titration rate or information controlling the timing of bolus deliveries. Patient 12 may use external programmer 20 to adjust the programs or groups of programs to regulate the therapy delivery.

Figure 2:
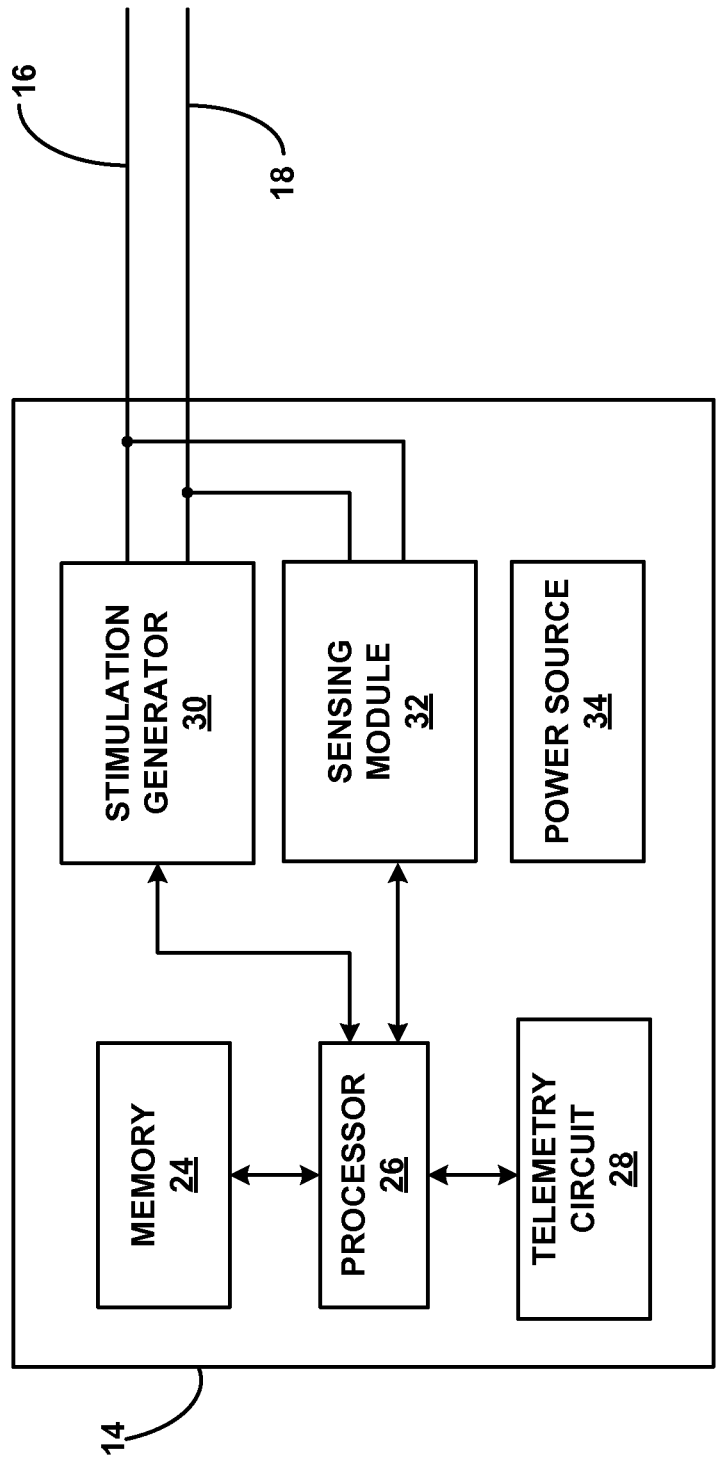
FIG. 2 is a functional block diagram illustrating various components of an example implantable electrical stimulator.

FIG. 2 is a functional block diagram illustrating various components of an IMD 14. In the example of FIG. 2, IMD 14 includes memory 24, processor 26, telemetry circuit 28, stimulation generator 30, sensing module 32, and power source 34. The stimulation generator 30 forms what may be referred to as a therapy delivery module.

Memory 24 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 24 may store instructions for execution by processor 26, stimulation therapy data, information regarding evoked signals sensed at one or more locations on the dorsal columns, and any other information regarding therapy or patient 12. Therapy information may be recorded for long-term storage and retrieval by a user, and the therapy information may include any data created by or stored in IMD 14. Memory 24 may include separate memories for storing instructions, sensed signal information, program histories, and any other data that may benefit from separate physical memory modules.

Memory 24 may be considered, in some examples, a non-transitory computer-readable storage medium comprising instructions that cause one or more processors, such as, e.g., processor 26, to implement one or more of the example techniques described in this disclosure. The term "non-transitory" may indicate that the storage medium is not embodied in a carrier wave or a propagated signal. However, the term "non-transitory" should not be interpreted to mean that memory 24 is non-movable. As one example, memory 24 may be removed from IMD 14, and moved to another device. In certain examples, a non-transitory storage medium may store data that can, over time, change (e.g., in RAM).

Processor 26 controls stimulation generator 30 to deliver electrical stimulation via electrode combinations formed by electrodes in one or more electrode arrays. For example, stimulation generator 30 may deliver electrical stimulation therapy via electrodes on one or more of leads 16 and 18, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be embodied as software, firmware, hardware, or any combination thereof.

Stimulation generator 30 may include stimulation generation circuitry to generate stimulation pulses or waveforms and switching circuitry to switch the stimulation across different electrode combinations, e.g., in response to control by processor 26. In particular, processor 26 may control the switching circuitry on a selective basis to cause stimulation generator 30 to deliver electrical stimulation to selected electrode combinations and to shift the electrical stimulation to different electrode combinations in a first direction or a second direction when the therapy must be delivered to a different location within patient 12. In other examples, stimulation generator 30 may include multiple current sources to drive more than one electrode combination at one time. In this case, stimulation generator 30 may decrease current to the first electrode combination and simultaneously increase current to the second electrode combination to shift the stimulation therapy.

An electrode configuration, e.g., electrode combination and associated electrode polarities, may be represented by a data stored in a memory location, e.g., in memory 24, of IMD 14. Processor 26 may access the memory location to determine the electrode combination and control stimulation generator 30 to deliver electrical stimulation via the indicated electrode combination. In some examples, the electrode configuration for delivery of dorsal column stimulation may be defined to deliver electrical stimulation to one or more particular locations identified based on an evaluation of signals evoked in the dorsal columns by peripheral and/or dorsal root stimulation. To adjust electrode combinations, amplitudes, pulse rates, or pulse widths, processor 26 may command stimulation generator 30 to make the appropriate changes to therapy according to instructions within memory 24 and rewrite the memory location to indicate the changed therapy. In other examples, rather than rewriting a single memory location, processor 26 may make use of two or more memory locations.

When activating stimulation, processor 26 may access not only the memory location specifying the electrode combination but also other memory locations specifying various stimulation parameters such as voltage or current amplitude, pulse width and pulse rate. Stimulation generator 30, e.g., under control of processor 26, then makes use of the electrode combination and parameters in formulating and delivering the electrical stimulation to patient 12.

An exemplary range of electrical stimulation parameters likely to be effective in treating chronic pain, e.g., when applied to dorsal column, dorsal root, and/or peripheral nerve locations, are listed below. Other stimulation parameter ranges are contemplated. While stimulation pulses are described, stimulation signals may be of any of a variety of forms such as sine waves or the like.

1. Pulse Rate: between approximately 0.5 Hz and approximately 1200 Hz, more preferably between approximately 5 Hz and approximately 250 Hz, and still more preferably between approximately 30 Hz and approximately 130 Hz.

2. Amplitude: between approximately 0.1 volts and approximately 50 volts, more preferably between approximately 0.5 volts and approximately 20 volts, and still more preferably between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.

3. Pulse Width: between approximately 10 microseconds and approximately 5000 microseconds, more preferably between approximately 100 microseconds and approximately 1000 microseconds, and still more preferably between approximately 180 microseconds and approximately 450 microseconds.

Processor 26 accesses stimulation parameters in memory 24, e.g., as programs and groups of programs. Upon selection of a particular program group, processor 26 may control stimulation generator 30 to generate and deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 26 also may control telemetry circuit 28 to send and receive information to and from external programmer 20.

Sensing module 32 may be configured to monitor one or more signals from one or more electrode on lead 16 and lead 18 in order to monitor electrical activity at one more locations in patient 12, e.g., via electrogram (EGM) signals. For example, sensing module 32 may be configured to monitor one or more electrical signals from electrode(s) on lead 18 at one or more dorsal column locations. Such electrical signals may be evoked by delivery of dorsal root stimulation and/or PNS by IMD 14. Signals sensed via a particular electrode may be made with reference to another electrode on a lead or an electrode on the housing of IMD 16. Sensing module 32 may also include a switch module to select which of the available electrodes, or which pairs or combinations of electrodes, are used to sense the activity evoked by dorsal root stimulation and/or PNS. In some examples, this disclosure describes techniques to support identification of dorsal column stimulation locations based on an analysis of stored information relating to sensed evoked signals.

In some examples, processor 26 may select the electrodes that function as sense electrodes via the switch module within sensing module 32, e.g., by providing signals via a data/address bus. Sensing module 32, in some cases, may be configured specifically for the purpose of sensing evoked signals. For example, sensing module 32 may include any combination of one or more different types of amplifiers configured for one or more specific types of sensing. Sensing module 32 may include a bank of different sense amplifiers specific to one or more sensed signals. The one or more separate amplifiers may be configured or programmable to perform one or more types of sensing.

Signals produced by the sense amplifiers may be converted from analog signals to digital signals by analog-to-digital converters (ADCs) provided by sensing module 32. The digital signals may be stored in memory for analysis on-board the IMD 14 or remote analysis by a programmer 20 or other device. Sensing module 32 may include a digital signal processor (DSP) that implements any of a variety of digital signal processing features such as digital amplifiers, digital filters, and the like. In general, the DSP may process the received signals to extract information useful in the evaluation of a signal for purposes of analyzing respective dorsal column locations as described herein. As an example, the DSP may determine a signal amplitude (current or voltage). Examples of other such information include but are not limited to waveform characteristics such as signal frequency, energy or power in one or more selected spectral bands, and other morphological characteristics, the relative area under a curve created by a sensed signal, the slope of a curve created by a sensed signal, inflection points of a curve created by a sensed signal, or various combinations of the foregoing information or similar information. Hence, the DSP may be configured to apply any of a variety of signal processing filters and algorithms to extract desired data from the sense signals, and also apply various statistical analysis algorithms to analyze particular dorsal column locations for stimulation.

In some examples, sensing module 32 includes one or more sensing channels, each of which may comprise an amplifier, as described above. In response to the signals from processor 26, the switch module within sensing module 32 may couple the outputs from the selected electrodes to one of the sensing channels.

Sensed signal data from sensing module 32 may be stored in memory 24 for later analysis by processor 26, review by a clinician, used to adjust therapy parameter (e.g., electrode combination), transmission to programmer 20 or other external device, or some combination thereof. As an example, processor 26 may record information associated with signals sensed at one or more locations on dorsal columns that are evoked by dorsal root stimulation and/or PNS and use the sensed signal information to determine a desirable location on the dorsal columns to deliver stimulation. In other examples, the sensed signal information may be transmitted to programmer 20 via telemetry circuit 28 for similar analysis. In this manner, IMD 14 and/or programmer 20 may be able to identify and maintain effective stimulation of the dorsal columns of patient 12.

IMD 14 wirelessly communicates with external programmer 20, e.g., a patient programmer or a clinician programmer, or another device by radio frequency (RF) communication or proximal inductive interaction of IMD 14 with external programmer 20. Telemetry circuit 28 may send information to and receive information from external programmer 20 on a continuous basis, at periodic intervals, at non-periodic intervals, or upon request from the stimulator or programmer. To support RF communication, telemetry circuit 28 may include appropriate electronic components, such as one or more antennas, amplifiers, filters, mixers, encoders, decoders, and the like.

Power source 34 delivers operating power to the components of IMD 14. Power source 34 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 3:
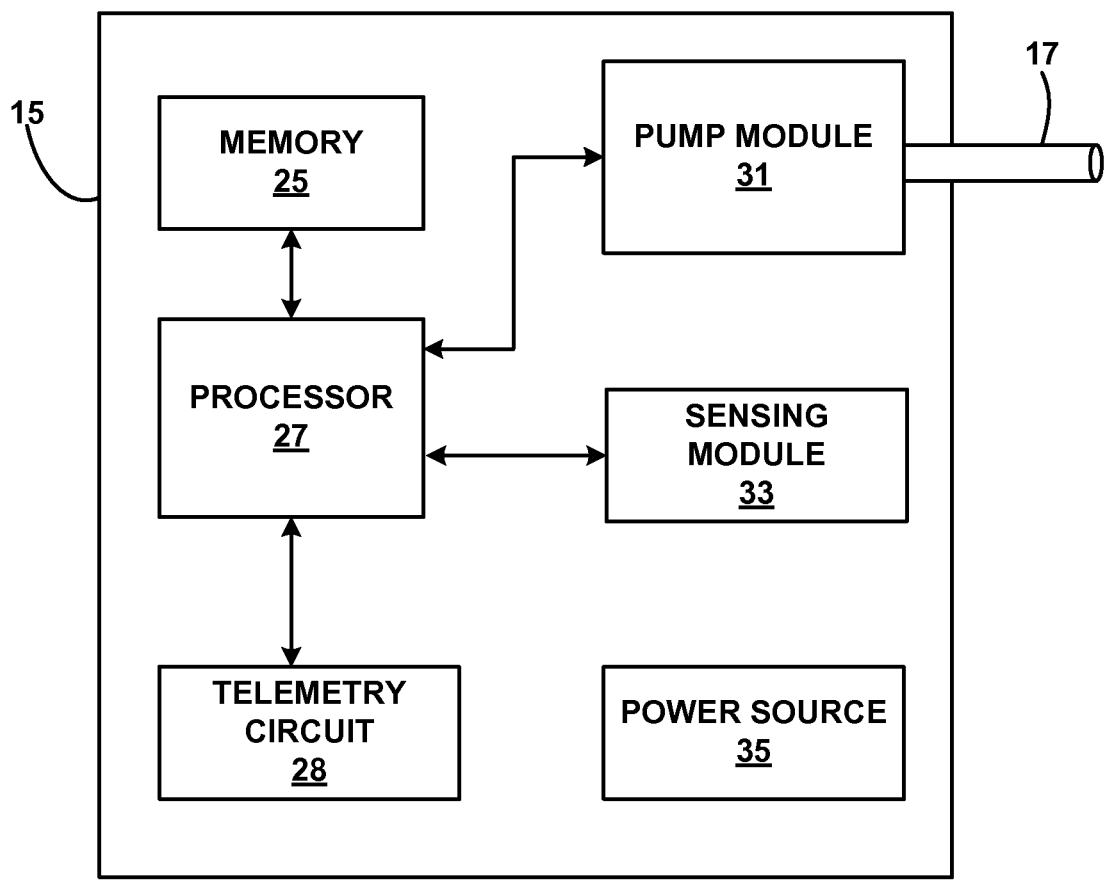
FIG. 3 is a functional block diagram illustrating various components of an example implantable drug delivery device.

FIG. 3 is a functional block diagram illustrating various components of an IMD 15, which delivers a therapeutic agent to patient 12. IMD 15 is a drug pump that operates substantially similar to IMD 14 of FIG. 2, but delivers a therapeutic agent instead of electrical stimulation. IMD 15 includes processor 27, memory 25, pump module 31, sensing module 33, telemetry circuit 28, and power source 35. Instead of stimulation generator 30 of IMD 14, IMD 15 includes pump module 31 for delivering drugs or some other therapeutic agent via catheter 17. Pump module 31 may include a reservoir to hold the drug and a pump mechanism to force the drug out of catheter 17 and into patient 12.

Processor 27 controls pump module 31 according to therapy instructions stored within memory 25. For example, memory 25 may contain the programs or groups of programs that define the drug delivery therapy for patient 12. A program may indicate the bolus size or flow rate of the drug, and processor 27 may accordingly deliver therapy. Processor 27 may also control pump module 31 to deliver drug therapy to the both the dorsal column(s) and dorsal root(s) of patient 12 in combination with one another.

Figure 4:
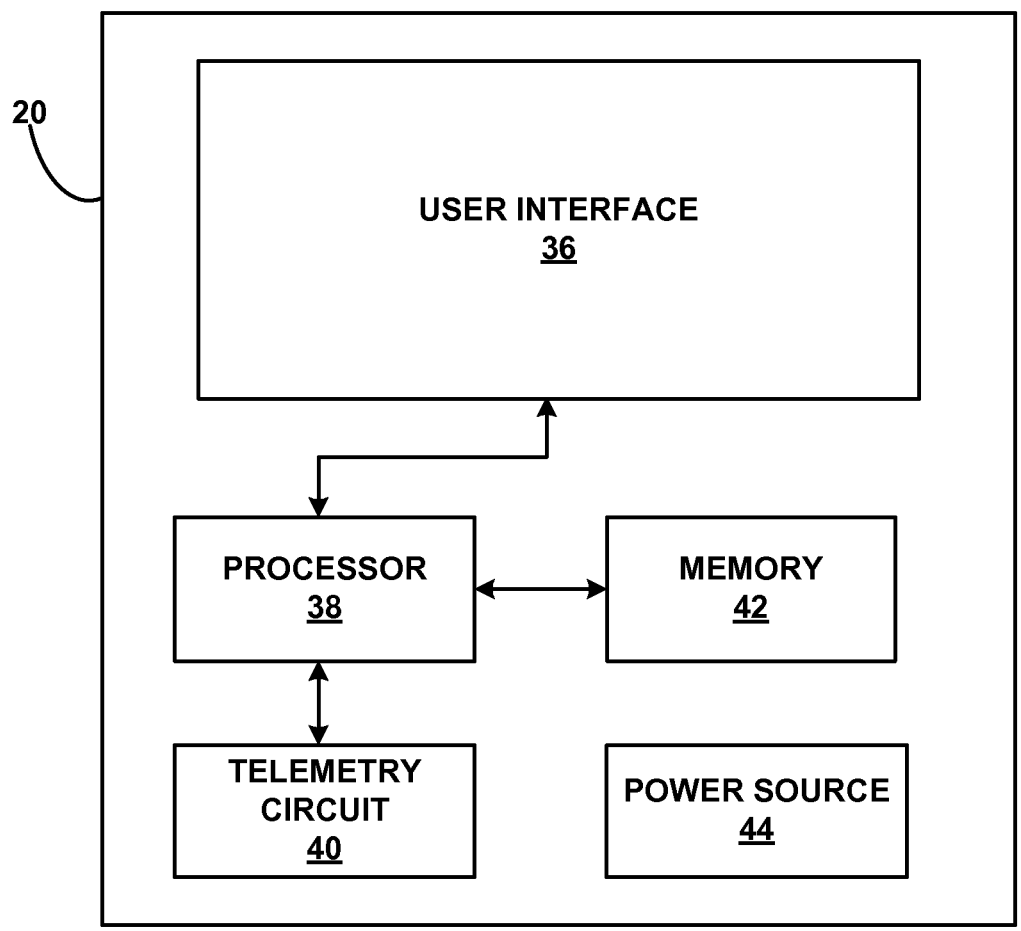
FIG. 4 is a functional block diagram illustrating various components of an example external programmer for an implantable medical device.

FIG. 4 is a functional block diagram illustrating various components of an external programmer 20 for IMD 14. Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming the IMD. As shown in FIG. 4, external programmer 20 includes user interface 36, processor 38, telemetry circuit 40, memory 42, and power source 44. External programmer 20 may be embodied as patient programmer or clinician programmer.

Processor 38 processes instructions by memory 42 and may store user input received through user interface 36 into the memory when appropriate for the current therapy. In addition, processor 38 provides and supports any of the functionality described herein with respect to each example of user interface 36. Processor 38 may comprise any one or more of a microprocessor, DSP, ASIC, FPGA, or other digital logic circuitry, and the functions attributed to programmer 38 may be embodied as software, firmware, hardware or any combination thereof.

Memory 42 may include any one or more of a RAM, ROM, EEPROM, flash memory or the like. Memory 42 may include instructions for operating user interface 36, telemetry module 40 and managing power source 44. Memory 42 may store program instructions that, when executed by processor 38, cause processor 38 and programmer 20 to provide the functionality ascribed to them herein. Memory 42 also includes instructions for generating and delivering programming commands to IMD 14. Memory 42 may also include a removable memory portion that may be used to provide memory updates or increases in memory capacities. A removable memory may also allow patient data to be easily transferred to another computing device, or to be removed before programmer 20 is used to program therapy for another patient.

Memory 42 may be considered, in some examples, a non-transitory computer-readable storage medium comprising instructions that cause one or more processors, such as, e.g., processor 38 and/or processor 26, to implement one or more of the example techniques described in this disclosure. The term "non-transitory" may indicate that the storage medium is not embodied in a carrier wave or a propagated signal. However, the term "non-transitory" should not be interpreted to mean that memory 42 is non-movable. As one example, memory 42 may be removed from IMD programmer 20, and moved to another device. In certain examples, a non-transitory storage medium may store data that can, over time, change (e.g., in RAM).

A clinician, patient 12, or another user (e.g., a patient caretaker) interacts with user interface 36 in order to manually change the stimulation parameter values of a program, change programs within a group, or otherwise communicate with IMD 14 or IMD 15.

User interface 36 may include a screen and one or more mechanisms, such as, buttons, as in the example of patient programmer 30, that allow external programmer 20 to receive input from a user. Alternatively, user interface 36 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information.

Processor 38 controls user interface 36, retrieves data from memory 42 and stores data within memory 42. Processor 38 also controls the transmission of data through telemetry circuit 40 to IMDs 14 or 26. Memory 42 includes operation instructions for processor 38 and data related to patient 12 therapy.

Telemetry circuit 40 allows the transfer of data to and from IMD 14 or IMD 15. Telemetry circuit 40 may communicate automatically with IMD 14 at a scheduled time or when the telemetry circuit detects the proximity of the stimulator. Alternatively, telemetry circuit 40 may communicate with IMD 14 when signaled by a user through user interface 36. To support RF communication, telemetry circuit 40 may include appropriate electronic components, such as amplifiers, filters, mixers, encoders, decoders, and the like. Power source 44 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter. Although not shown in FIG. 4, in some examples, external programmer 20 may include a charger module capable of recharging a power source, such as a rechargeable battery that may be included in power source 34 of IMD 14. Hence, in some cases, the programmer may be integrated with recharging components to form a combined programmer/recharger unit.

FIG. 5 is a conceptual diagram illustrating an example implantable stimulation system 46 for delivering stimulation to patient 12. In particular, system 46 may deliver stimulation to one or more dorsal column locations, one or more dorsal roots, and/or peripheral nerve(s). Implantable stimulation system 46 includes IMD 14, leads 48 and 50, and may be the same or substantially similar to stimulation system 10 (FIG. 1) except leads 48 and 50 may differ in one or more aspects from that of leads 16 and 18. For example, as shown, lead 48 has a trifurcated distal end and is implanted proximate to one or more locations along the dorsal columns and one or more dorsal roots of patient 12. In this manner, IMD 14 may deliver both dorsal column stimulation and dorsal root stimulation to patient 12 via lead 48. For example, IMD 14 may deliver stimulation via one or more electrodes on lead 48 to a dorsal root at first location 52, and may also deliver stimulation via one or more electrodes of lead 48 at dorsal columns locations 56A, 56B, 56C, and 56D. Additionally, IMD 14 delivers PNS to patient 12 via one or more electrodes on lead 50 at second location 54. In other examples, multiple, separate leads may deliver electrical stimulation to patient 12 at one or more locations.

In accordance with some aspects of the disclosure, a particular location on the dorsal columns, e.g., one or more dorsal column locations associated with pain, may be identified based on the analysis of one or more parameters of signals sensed, e.g., via sensing module 32 (FIG. 2), at one or more locations on the dorsal columns. The sensed signals may be evoked via the delivery of electrical stimulation to one or more dorsal roots and/or peripheral nerves.

Figure 6:
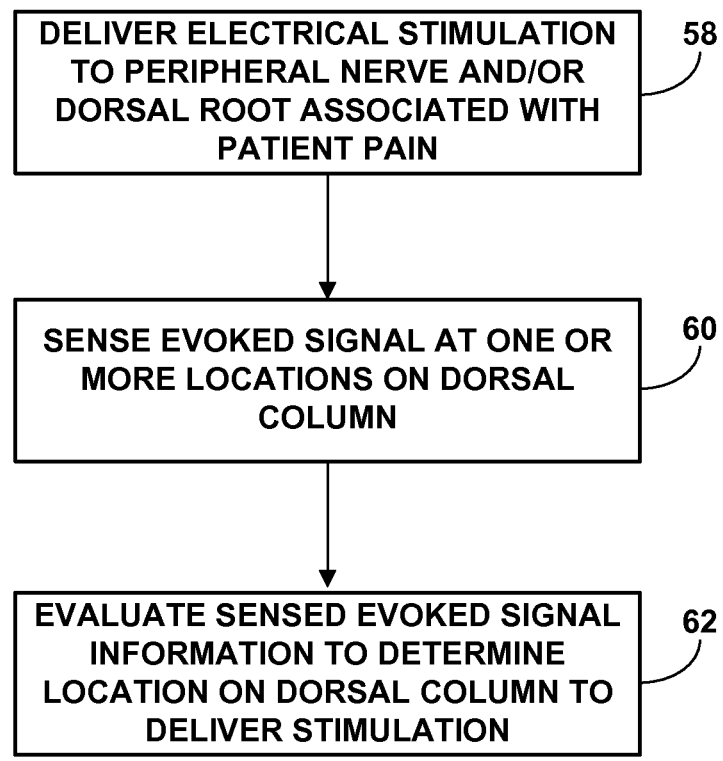
FIG. 6 is a flow diagram illustrating an example technique for identifying one or more particular locations on the dorsal columns for delivery of stimulation therapy.

FIG. 6 is a flowchart illustrating an example technique for identifying one or more particular locations on the dorsal columns for delivery of stimulation therapy. For purposes of illustration, the technique of FIG. 6 is described with regard to implantable stimulation system 46 (FIG. 5). However, such a technique may be incorporated into any suitable device or system that delivers stimulation to one or more locations on the dorsal columns of a patient.

In the example of FIG. 6, upon direction by clinician via programmer 20 or on an automatic or semi-automatic basis, IMD 14 delivers electrical stimulation to a dorsal root at first location 52 and/or a peripheral nerve at second location 54 via one or more electrodes on leads 48 and 50, respectively (58). The particular dorsal root and peripheral nerve may be known to be associated with the area of pain intended to be treated by stimulation of the dorsal columns. For example, stimulation of the particular dorsal root and/or peripheral nerve at first and second locations 52 and 54, respectively, may result in a sensation in the area of pain experienced by patient 12. In some examples, delivery of stimulation to first location 52 and/or second location 54 may provide effective pain relief for patient 12. However, for one or more reasons, it may also be desirable to treat the pain with dorsal column stimulation in addition to or as an alternative to delivery of stimulation to first and/or second locations 52 and 54. In general, any suitable techniques may be utilized to identify particular peripheral nerves and/or dorsal root associated with a particular patient condition. Although not limited to such guidelines, dorsal root stimulation may be more effective for generalized pain, since dorsal roots may be associated with larger areas of the body, while PNS may be more effective in cases in which the pain experienced by patient 12 is more localized. In some examples, the peripheral nerve corresponding to the second location 54 and the dorsal root corresponding to the first location 52 share a common nerve fiber or group of nerve fibers. While examples of the disclosure are primary described with regard to delivery of therapy, e.g., electrical stimulation therapy, to treat or manage pain experienced by patient 12, examples are not limited to the treatment of management of patient pain. In general, examples may include any patient condition that may be treated and/or managed via delivery of therapy as described in the disclosure.

IMD 14 delivers stimulation to first location 52 and/or second location 54 in a manner that evokes one or more signals at one or more locations on the dorsal columns of patient 12 (58). For example, the stimulation delivered to first location 52 and/or second location 54 may activate one nerve fiber or a group of nerve fibers of the dorsal root and/or peripheral nerve, respectively. In some examples, the stimulation parameters may be the same or substantially similar to that which results in stimulation sensation of the area of pain to be treated, or stimulation that provides effective relief to patient 12 from the pain. In some examples, the stimulation delivered by IMD 14 may be a series of pulses configured to evoke one or more signals in the dorsal column, which may or may not be stimulation which innervates or treats the area of pain experienced by patient 12. IMD 14 may deliver stimulation pulses to first location 52 and/or second location 54 having an amplitude that a patient can tolerate (e.g., between approximately 1 and approximately 10 volts). The stimulation signal may be delivered at a relatively low frequency. For example, IMD 14 may generate and deliver stimulation pulses to first location 52 and/or second location 54 at a frequency of less than 10 Hz, such as, e.g., approximately 4 to approximately 6 Hz. Other stimulation parameters are contemplated. In examples in which IMD 14 delivers stimulation to both first and second locations 52 and 54, the stimulation delivered to first location 52 may be substantially the same as that delivered to second location 54, or the stimulation delivered to first location 52 may be different from that delivered to second location 54.

In any case, IMD 14 delivers stimulation to first location 52 and/or second location 54 in a manner that evokes one or more signals at one or more locations on the dorsal columns of patient 12 (58). For example, the activation of the nerve fiber or group of nerve fibers at first location 52 and/or second location 54 generates a signal (e.g., compound action potential) that may propagates from the dorsal root and/or peripheral nerve along the nerve fiber or group of nerve fiber to the dorsal columns. In conjunction with the delivery of dorsal root stimulation and/or PNS to first and second locations, respectively, sensing module 32 of IMD 14 senses one or more signals evoked by the delivery of the dorsal root stimulation and/or PNS to patient 12 (60). For example, as illustrated in FIG. 5, sensing module 32 may monitor for evoked signals at each of locations 56A-D on the dorsal columns of patient 12 via one or more electrodes on lead 48. Assuming conduction is occurring between the location at which the stimulation is being delivered (first location 52 and/or second location 54) and the at least one or more locations 56A-D on the dorsal columns, an evoked signal will be sensed by sensing module 32 at one or more of locations 56A-D that roughly corresponds to the generated pulses. For instance, if IMD 14 is generating and delivering stimulation pulses at first location 52 and/or second location 54, the signal sensed at one or more of locations 56A-D may exhibit characteristics, such as, evoked potentials (e.g., "blips") that roughly correspond to the delivered stimulation pulses. Signal "blips" may correspond to action potentials evoked in nerve fibers at one or more locations in the dorsal columns by the delivery of stimulation pulses to the first location 52 and second location 54. Since the evoked signal propagates along the nerve fiber or group of nerve fibers stimulated at the first location 52 and/or second location 54, the sensed evoked signal may be used to identify the location of the same nerve fiber or group of nerves fibers within the dorsal columns of patient 12. In some examples, the amplitude the sensed evoked signal may be a voltage amplitude that is relatively small (e.g., on the order of millivolts (mV)), and sensing module 32 may be configured to suitably sense such signals (e.g., by adjusting amplifier gain). IMD 14 may store the information regarding the sensed evoked signal at each dorsal column location 56A-D (e.g., amplitudes of sensed evoked signal) in memory 24 (FIG. 2) for evaluation by processor 26.

Processor 26 of IMD 14 (or processor 38 of programmer 20) may evaluate the sensed signal information to determine the particular location on the dorsal columns for delivery of stimulation (62). In some examples, processor 26 may evaluate the amplitude of evoked signal sensed at each respective dorsal columns location 56A-D to identify the location 56A-56 at which the greatest amplitude was sensed by sensing module 32. The location yielding the largest signal amplitude may be selected by IMD 14 as the location on the dorsal columns out of all of locations 56A-D that may provide optimal or at least the most effective treatment of the pain experienced by patient 12. In some examples, IMD 14 may present the location yielding the largest signal amplitude to a clinician via programmer 20, e.g., for the clinician approval of the respective location for dorsal column stimulation.

As an illustration, based on an evaluation of the sensed evoked signal information, processor 26 may determine that location 56B yielded the greatest signal amplitude out of all of locations 56A-D. In such a case, IMD 14 may then be programmed to generate and deliver stimulation to location 56B on the dorsal columns. To deliver stimulation to location 56B after processor 26 has identified it as the location yielding the greatest evoked signal amplitude, IMD 14 may deliver stimulation to location 56B via the same electrodes on lead 48 used to sense the evoked signal at that location on the dorsal columns. In other examples, one or more electrodes other than that used to sense evoked signal may be used to deliver therapy to the dorsal columns.

The delivery of stimulation to location 56B via the same electrode(s) used to sense the evoked signal (or via other electrode(s) configured to deliver stimulation to location 56B) may activate the same group of fibers that were stimulated through the dorsal root stimulation and/or peripheral nerve stimulation. Examples are not limited to indentifying a single dorsal column stimulation location based on the sensed evoked signals. For example, IMD 14 may identify two dorsal column stimulation locations based on the sensed evoked signals, e.g., the sensed locations with the two highest amplitude values.

In some examples, sensing module 32 may sense evoked signals at each location 56A-D for a predetermined amount of pulses delivered to first location 52 and/or second location 54. For example, sensing module 32 may sense evoked signals at each location corresponding to the delivery of approximately 50 to approximately 1000 pulses to first location 52 and/or second location 54. Based on the sensed evoked signals, processor 26 may determine an average amplitude value (or other statistically significant value) of the evoked signal sensed at each location 56A-56D. The evoked signal at each respective location may be sensed via one or more electrodes at the location. The one or more electrodes at each location may be referenced back to a reference electrode on a lead, e.g., lead 48, (bipolar sensing) or an electrode on the housing of IMD 14, e.g., a can electrode, (unipolar sensing). IMD 14 may select one or more of locations 56A-D for delivery of stimulation based on the average amplitude value, or other suitable signal parameter, determined for each respective location.

As described above, sensing module 32 may sense the evoked signals at locations 56A-D via one or more electrodes on lead 48. Sensing module 32 may sense at locations 56A-D serially or in parallel as stimulation generator 30 delivers stimulation to first location 52 and/or second location 54. For example, sensing module 32 may sense evoked signals at all of locations 56A-D at substantially the same time or sensing module 32 may sense evoked signal at locations 56A-D individually. In some case, sensing module 32 may sense at more than but not all of locations 56A-D at substantially the same time. In each example, an average amplitude value for the sensed evoked signals may be determined for each location 56A-D, and IMD 14 may select a particular location for delivery of dorsal column stimulation based on the average evoked signal amplitude determined for each location.

Dorsal column locations 56A-D may be evaluated for delivery of dorsal column stimulation based on any combination of signals evoked from stimulation of first location 52

(dorsal root stimulation) and second location 54 (PNS). For example, processor 26 may evaluate locations 56A-D based on sensed signals evoked by delivery on stimulation to first location 52. Similarly, processor 26 may evaluate locations 56A-D based on sensed signals evoked by delivery on stimulation to second location 54. Alternatively, processor 26 may evaluate locations 56A-D based on sensed signals evoked by stimulation delivered substantially simultaneously to both first and second locations 52 and 54.

In some examples, sensing module 32 may sense signals evoked from stimulation at first location 56 for a predetermined number of pulses. Once complete, IMD 14 may terminate stimulation at first location 52 and begin delivery of stimulation to second location 56, at which point sensing module 32 may sense signals evoked from stimulation at second location 54 for a predetermined number of pulses. Processor 26 may then evaluate respective locations 56A-D based on the overall average amplitude value of all the sensed evoked signals. For example, processor 26 may identify the respective location exhibiting the largest overall average amplitude value as the location to deliver dorsal column stimulation. The delivery of stimulation to evoke signals in the dorsal columns is not limited to single dorsal root locations and/or single peripheral nerve locations, but may include multiple dorsal root locations and/or multiple peripheral nerve locations, which may be stimulated simultaneously, individually or some combination thereof.

While locations 56A-D are illustrated in FIG. 6 as extending longitudinally along the dorsal columns, examples are not limited to such an orientation. IMD 14 may be configured to sense evoked signals a plurality of locations on the dorsal columns to evaluate the respective locations for delivery of dorsal column stimulation. In general, the sensed locations may extend in any direction relative the dorsal columns. In some examples, the sensed locations may extend across the dorsal columns in addition to or as an alternative to extending in the longitudinal direction. In this manner, one or more particular dorsal column stimulation locations can be targeted based on sensed evoked potentials at locations at any point on the dorsal column (e.g., with the locations arranged longitudinally, across, or some combination thereof on the distal columns).

In some examples, rather than evaluating the sensed evoked signals for each of locations 56A-D relative to one another to identify a particular dorsal column stimulation location, one or more properties of a sensed signal may be evaluated with regard to predefined values, e.g., threshold amplitude values, to identify a particular dorsal column stimulation location. For example, sensing module 32 may sense evoked signals at location 56A in conjunction with the delivery of stimulation to first location 52. If the sensed evoked signal has an amplitude value greater than a minimum threshold amplitude value defined for dorsal column stimulation, for example, then processor 26 may identify location 56A as a target location for dorsal column stimulation. In some examples, processor 26 may use such criteria in addition to comparison of the sensed evoked signals at multiple sites to identify target dorsal column stimulation location. For example, processor 26 may identify location 56A as a viable dorsal column stimulation location only if evoked signal sensed at location 56A exhibited the greatest amplitude value and the amplitude value was greater than a minimum threshold amplitude value. In some examples, processor 26 may evaluate and/or identify more than one location if each location satisfies some threshold, e.g., two locations exhibit an amplitude greater than a minimum amplitude threshold.

In some examples, processor 26 may additionally or alternatively evaluate each of locations 56A-D based on the conduction times, i.e., the delay between a stimulation signal being delivered to first location 52 and/or second location 54 and the receipt of the corresponding evoked signal at a respective location on the dorsal columns. Conduction times may be indicative of the optimal or most effective location of the dorsal column for stimulation relative the one or more locations evaluated. Accordingly, processor 26 may evaluate locations 56A-D based on sensed conduction times and identify the respective location on dorsal column which exhibited the shortest average conduction time as the location for delivery of dorsal column stimulation. In some examples, processor 26 may evaluate the respective locations 56A-56D based on both sensed signal amplitude and conduction times. For example, processor 26 may select a particular dorsal column location for delivery of stimulation using a formula which effectively assigns a particular weight to each metric (amplitude and conduction time) and computes an overall score for each respective location 56A-56D. Processor 26 may identify the location with the highest overall score as the preferred dorsal column stimulation location.

In some examples, processor 26 may additionally or alternatively evaluate each of locations 56A-D based on one or more characteristics of the evoked signals. For example, while the examples described herein may describe evaluating each location based at least in part on the amplitude of sensed evoked signals, processor 26 may evaluate each location based on other signal information. Examples of other such information may include but are not limited to waveform characteristics such as signal frequency, energy or power in one or more selected spectral bands, and other morphological characteristics, the relative area under a curve created by a sensed signal, the slope of a curve created by a sensed signal, inflection points of a curve created by a sensed signal, or various combinations of the foregoing information or similar information. In some examples, processor 26 may select the dorsal column location exhibiting the largest area under the curve created by the sensed evoked signal as the particular location for delivery of dorsal column stimulation.

In some examples, processor 26 may evaluate dorsal column locations that have been identified for stimulation in view of patient input. For example, once one or more dorsal column locations have been selected based on the sensed signal evoked from dorsal root and/or peripheral nerve stimulation, IMD 14 may deliver stimulation to the dorsal column location(s) during a trial period. Patient 12 may indicate to IMD 14 (e.g., via programmer 20) whether the stimulation during the trial period effectively treated the area of pain. If patient 12 indicates that the dorsal column stimulation was effective, IMD 14 may continue to deliver stimulation to the identified location(s) on the dorsal columns. Conversely, if patient 12 indicates that the dorsal column stimulation was ineffective in treating the pain, IMD 14 may terminate delivery of dorsal column stimulation and identify one or more new dorsal column stimulation locations, e.g., by repeating the process of identifying particular stimulation location(s) on the dorsal columns based on sensed evoked signals. In this manner, patient input may be used to validate the dorsal column location selected for stimulation based on sensed signal evoked from dorsal root and/or peripheral nerve stimulation, as described herein.

The example technique of FIG. 6 may be useful for identifying one or more particular locations on the dorsal columns to deliver stimulation to treat patient pain or other patient conditions. For example, dorsal column locations 56A-D may be located in a general area of the dorsal columns that is thought to roughly correspond to the dorsal root and/or peripheral nerve stimulated at first and second locations 52 and 54, respectively. Based on one or more properties of the sensed evoked signals (e.g., signal amplitude) at each respective location, IMD 14 may to identify one or more particular locations from locations 56A-D for delivery of electrical stimulation that effectively treats pain experienced by patient 12. Such a technique may reduce the programming burden by locating appropriate electrodes for dorsal column stimulation in a manner that does not require significant amounts of trial and error based on patient feedback. Such a process may also be performed while the patient completely sedated, if desired, since such a process does not rely on patient feedback.

The example technique of FIG. 6 may be used to position lead 48 relative to the dorsal columns of patient in conjunction with implantation of lead 48 within patient 12. For example, a clinician may determine particular locations on the dorsal columns for effective stimulation based on the sensed signals evoked by stimulation of first location 52 and/or second location 54. During implantation, a clinician may initially position lead 48 within patient 12 such that one or more electrodes are proximate to the dorsal columns. Once positioned, sensing module 32 may sense evoked signals via delivery of dorsal root stimulation or PNS (delivered by IMD 14 or external trial stimulator device), and monitor the evoked signals at one or more locations of the dorsal column via one or more electrodes on lead 48, as described above. In some examples, the clinician may obtain the sensed evoked signal information from IMD 14 via programmer 20. Processor 38 (FIG. 4) in programmer 20 may evaluate the sensed signal by identifying the location corresponding to the greatest sensed amplitude, or may evaluate the sensed signal information by displaying the sensed signal information to the clinician via user interface 36 (FIG. 4). Depending on the amplitude of the sensed evoked signals, the clinician may manually, or with the assistance of a suitable automated mechanism, reposition lead 48 relative to the dorsal columns to allow for sensing of evoked signals at one or more new locations on the dorsal columns. Such a process may be repeated until lead 48 is positioned relative to the dorsal columns in a manner that allows for effective stimulation of the dorsal columns via one or more electrodes located on the lead 48.

As an illustration, if the L2 root (not labeled in FIG. 5) is stimulated by IMD 14, the evoked signal may be sensed via one or more electrodes positioned farther rostral or caudal in the spinal cord. The location at which the evoked signal is sensed may be moved (e.g., by physically moving lead 48 relative to the dorsal columns) more medial or lateral, or even rostral or caudal, to identify the location on the dorsal columns where the greatest evoked signal amplitude is sensed, e.g., via sensing module 32. Once such a location has been identified, IMD 14 may deliver dorsal column stimulation to the location via the same electrodes used to sense the evoked signal at that respective location to activate the same group of fibers that were stimulation through the L2 root stimulation. Such a process may allow for more precise targeting of proper dorsal column fibers.

In some examples, lead 48 may form all or a part of an array of electrodes (e.g., an 8×8 electrode array) that allows sensing module 32 to sense evoked signals at a plurality of dorsal column locations using the electrode array. As one example, lead 48 may include two separate leads each with eight electrodes which form an array capable of sensing evoked signals at a plurality of distal column locations. In such an example, in addition to or as an alternative to physically moving lead 48 relative to the dorsal columns, IMD 14 may utilize the technique of FIG. 6 to identify particular electrode combinations for delivery of stimulation to a particular location identified based on an evaluation of the sensed evoked signals. In this manner, the programming burden associated with identifying one or more appropriate locations for dorsal column stimulation may be reduced.

Once one or more particular locations of the dorsal columns are identified by monitoring signals evoked on the dorsal columns by dorsal root stimulation and/or PNS, the leads used to deliver dorsal root stimulation and/or PNS to patient 12 from IMD 14 or other suitable medical device may be removed from patient 12. For example, if the dorsal root stimulation and/or PNS is delivered from an external trial stimulation to patient 12 via one or more percutaneously implanted leads, such leads may be removed from patient 12 after identification of one or more particular dorsal column locations based on sensed evoked signals as described herein. In other examples, the one or more leads may remain in patient 12, e.g., to deliver PNS or dorsal root stimulation in combination with the dorsal column stimulation.

Application of the example technique of FIG. 6 is not limited to identifying one or more particular dorsal column stimulation locations in conjunction with a procedure to implant lead 48 within patient 12. In some examples, even after one or more particular dorsal column locations have been identified for delivery of effective stimulation, IMD 14 may utilize such a technique to maintain the effectiveness of the dorsal column stimulation delivered to patient 12 for treating patient pain or other symptoms. In some cases, lead migration may cause one or more electrodes on lead 48 to move relative to the dorsal columns of patient 12. Additionally, while the position of the one or more electrodes relative to the dorsal columns may stay substantially the same over time, physiological factors may cause the particular location on the dorsal columns for optimal treatment via electrical stimulation to migrate to one or more other locations on the dorsal columns. In each case, the therapeutic efficacy of the electrical stimulation delivered to a particular location on the dorsal column of the patient may be negatively influenced.

Accordingly, IMD 14 may be configured to automatically or semi-automatically adjust the particular stimulation location on the dorsal columns based on signals evoked via dorsal root stimulation and/or PNS. For example, IMD 14 may be programmed to recalibrate the stimulation location by reevaluating one or more available stimulation locations on the dorsal columns using a technique the same or similar to that of FIG. 6 even after a particular dorsal column stimulation location has been identified previously. In some examples, IMD 14 may be configured to carry out such a process on a periodic basis or based on patient or clinician input received via programmer 20. In such examples, IMD 14 may utilize the technique of FIG. 6 to determine whether or not the current dorsal column stimulation location is still the preferred location based on the evaluation of the sensed evoked signals. If the sensed evoked signals indicate that the present dorsal column stimulation location is no longer most preferred (e.g., no longer exhibits the greatest evoked signal amplitude), then IMD 14 may automatically adjust the electrode combination in accordance with the presently sensed evoked signals, prompt a patient or clinician via programmer 20 for permission to make such an adjustment, and/or alert a patient or clinician of the detected scenario so that it may be properly addressed.

As described above, some examples of the disclosure relate to delivery of dorsal column stimulation in combination with the delivery of dorsal root stimulation. While dorsal column stimulation may provide excellent pain relief for a number of patient conditions (e.g., CRPS, angina pectoris, neuropathic pain, and failed back surgery syndrome), dorsal column stimulation may not always provide complete or consistent pain relief and/or coverage for particular patient areas and condition, such as, e.g., lower back, buttock, feet, groin, pelvis, and neck. PNS may treat such cases but also has limitations, including, e.g., access to stimulation locations and/or lead migration. However, unlike PNS, dorsal root and/or dorsal column stimulation leads may be located along the relatively stable and immobile spinal cord 22. Examples illustrating one or more aspects related to the delivery of dorsal column stimulation in combination with the delivery of dorsal root stimulation are described with reference to implantable stimulation system 10 (FIG. 1). However, examples are not limited to such therapy systems.

As previously described, IMD 14 may deliver dorsal column stimulation to patient 12 via one or more electrodes on lead 18. In combination with the delivery of dorsal column stimulation to patient 12, IMD 14 may deliver stimulation to one or more dorsal root locations via one or more electrodes on lead 16. In some examples, the dorsal column stimulation may be delivered in combination with the dorsal root stimulation to treat substantially the same patient condition, e.g., to treat the same pain type or origin of pain experienced by a patient, while in other examples, the dorsal column and dorsal stimulation may treat different or unrelated patient conditions, e.g., the dorsal column stimulation may treat a first pain type or origin of pain experienced by patient 12 while the dorsal root stimulation may treat a second pain type or origin of pain. The particular location(s) on the dorsal column may be identified using a technique that is the same or substantially similar to that of the example technique of FIG. 6. In such cases, IMD 14 may deliver dorsal root stimulation to substantially the same dorsal root location that was used to evoke signals in the dorsal column for identification of the dorsal column location for stimulation. In some examples, IMD 14 may deliver stimulation to multiple dorsal column locations and/or multiple dorsal root locations. By delivering dorsal column stimulation and dorsal root stimulation in combination with one another, the effectiveness of the multi-site, coordinated stimulation in treating a patient's pain may be greater than that achieved by delivering only dorsal columns stimulation or only dorsal root stimulation to patient 12.

In some cases, based at least in part on physiological differences at dorsal root and dorsal column location, the optimal or effective stimulation parameters of stimulation delivered to a dorsal root location may be different than the stimulation parameters. As such, IMD 14 may deliver stimulation to the dorsal root of patient 12 according to different set of therapy parameter values (e.g., amplitude, frequency, wave form, and the like) from that of the dorsal column stimulation delivered to patient 12. For instance, different therapy programs may define stimulation parameters for each of the dorsal column stimulation and dorsal root stimulation, and different channels may be used to drive the stimulation signal at respective locations. In other examples, IMD 14 may deliver the dorsal column stimulation and dorsal root stimulation according to substantially the same stimulation parameters.

FIGS. 7A-7F are timing diagrams illustrating examples of delivery of dorsal column stimulation in combination with dorsal root stimulation. In general, with reference to FIG. 1A for purposes of illustration, IMD 14 may deliver electrical pulses via leads 18 and 16, respectively, according to each of the therapies simultaneously, in an interleaved or alternating fashion, or overlapping in some degree in time. For example, each electrical stimulation therapy may have different pulse rates, duty cycles, waveforms or scheduled times for delivery, or IMD 14 may deliver programs of a program group in an interleaved fashion, each of which may result in an alternating delivery of the therapies. The timing of stimulation relative to one another, and general delivery of dorsal column stimulation in combination with dorsal root stimulation, may combat issues that can arise from the exclusive delivery of stimulation to one location, such as fatigue, intolerance, discomfort and tolerance. In each of FIGS. 7A-7F, the top group of pulses represents delivery of dorsal column stimulation pulses by IMD 14, and the bottom group of pulses represents delivery of dorsal root stimulation pulses. Each group of pulses may represent delivery of pulses by IMD 14 according to a respective therapy program, and both groups of pulses may be included in a common program group.

Figure 7A:
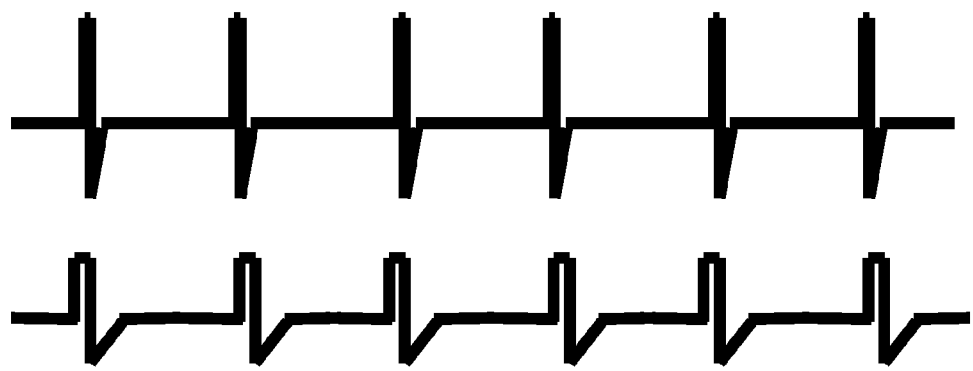
FIGS. 7A-7F are example timing diagrams illustrating delivery of dorsal column stimulation in combination with dorsal root stimulation.

FIG. 7A illustrates simultaneous delivery of dorsal column stimulation and dorsal root stimulation using a common pulse rate by IMD 14. However, the dorsal column stimulation and dorsal root stimulation are delivered with different amplitudes and pulse widths. Specifically, in the example illustrated by FIG. 7A, the pulses for the dorsal column stimulation have greater amplitude and shorter pulse widths than the pulses delivered for the dorsal root stimulation.

Figure 7B:
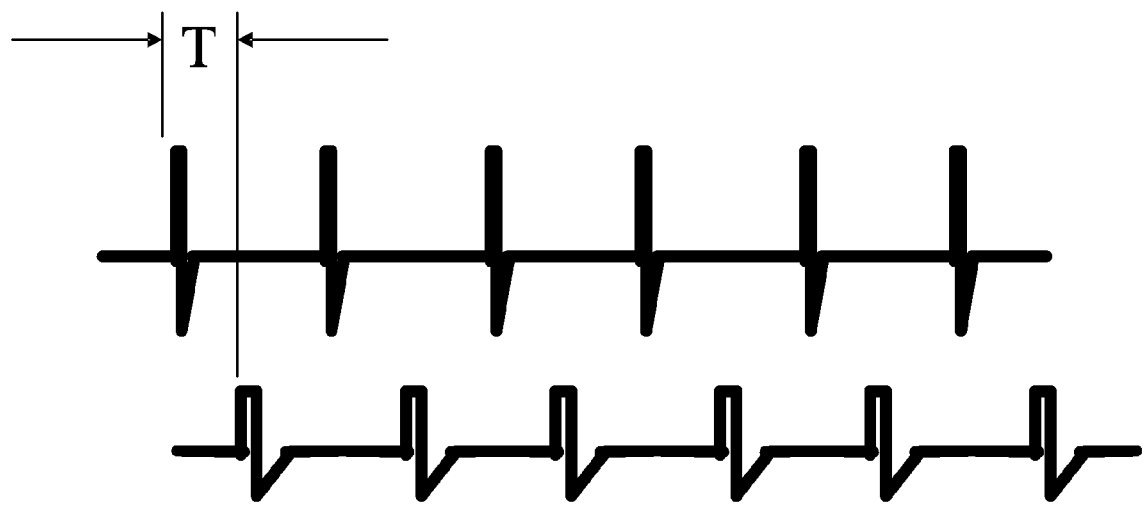

FIG. 7B illustrates interleaved delivery of dorsal column stimulation and dorsal root stimulation by IMD 14 at the common pulse rate and different pulse amplitudes and widths illustrated by FIG. 7A. Interleaved delivery of dorsal column pulses and dorsal root pulses result in a phase offset represented by a time T.

Figure 7C:
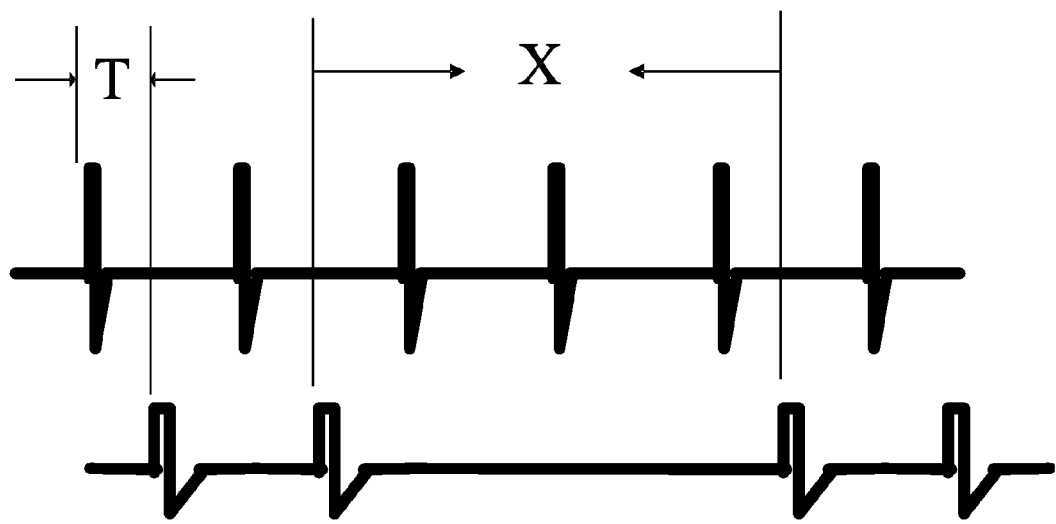

As was the case with FIG. 7B, FIG. 7C illustrates interleaved delivery of dorsal column stimulation and dorsal root stimulation by IMD 14 at the common pulse rate and different pulse amplitudes and widths illustrated by FIG. 7A. However, in the example illustrated by FIG. 7C, IMD 14 delivers dorsal root stimulation according to a duty cycle, rather than continuously. As a result, the dorsal column stimulation and dorsal root stimulation are delivered in an interleaved fashion similar to FIG. 7B for a period of time, followed by an equal period of time in which only the dorsal column is delivered.

Figure 7D:
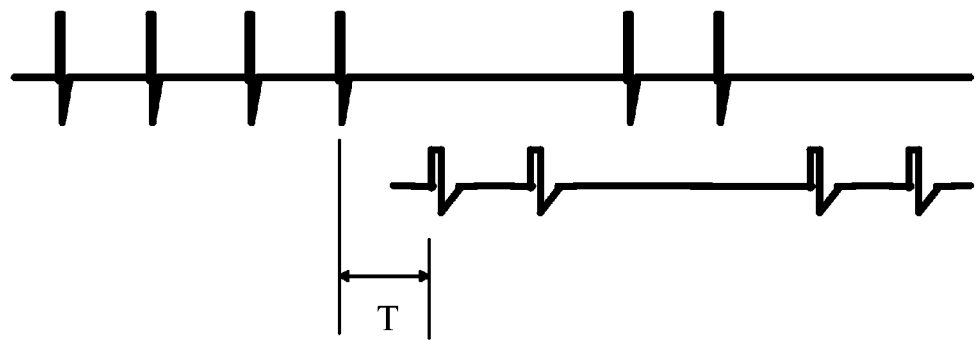

FIG. 7D illustrates delivery of both dorsal column stimulation and dorsal root stimulation according to respective duty cycles, where the duty cycles result in alternating delivery of dorsal column stimulation and dorsal root stimulation. For example, IMD 14 may deliver dorsal root stimulation for a particular time period, e.g., one hour, and then delivery dorsal column stimulation for a particular time period, e.g., one hour.

Figure 7E:
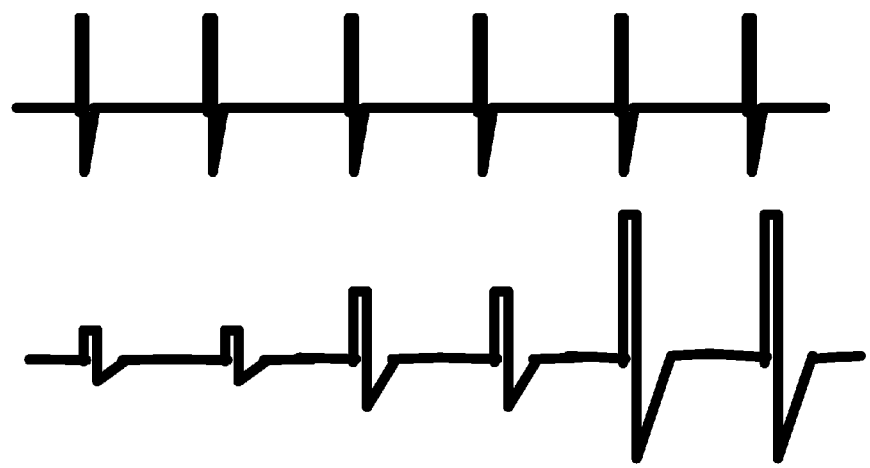

FIG. 7E illustrates an example in which IMD 14 increases, e.g., "ramps up," the pulse amplitude of the dorsal root stimulation over time. In particular, FIG. 7E illustrates a pulse amplitude increase every two pulses. Additionally or alternatively, pulse amplitudes may be may be incrementally decreased, e.g., "ramped down," over a period of time that the stimulation is delivered to patient 12.

Figure 7F:
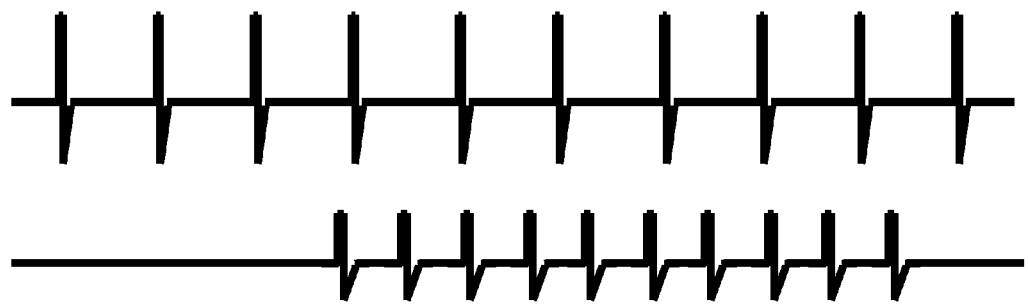

FIG. 7F illustrates delivery of dorsal column simulation and dorsal root stimulation therapy by IMD according to different therapy parameters. In particular, IMD 14 delivers pulses for dorsal column stimulation at a frequency, amplitude, and pulse width that is different from that of the frequency, amplitude, and pulse width of the dorsal root stimulation. In some examples, IMD 14 may deliver the dorsal column stimulation according to a first therapy program and deliver the dorsal root stimulation according to a second therapy program different from the first. In other examples, dorsal column stimulation may be delivered using a different pulse shape or waveform than that used to deliver dorsal root stimulation. For instance, dorsal column stimulation may be delivered as a pulse train similar to that shown in any of FIGS.

7A-7F, whereas dorsal root stimulation may be delivered using a sine wave or other waveform.

The type of stimulation delivered to the dorsal column and/or dorsal root from IMD 14 may be automatically, semi-automatically, or manually adjusted based on one or more variables. In some examples, IMD 14 may automatically or semi-automatically adjust the type of stimulation delivered to the dorsal column and the dorsal root based on time (e.g., time of day, week, month or the like). For example, IMD 14 may adjust one or more stimulation parameters (e.g., frequency, amplitude, pulse width) of the respective stimulations and/or may adjust the timing or other aspects of the respective stimulations with regard to one another. IMD 14 may also adjust the therapy delivery to patient 12 by modifying the site (dorsal column/dorsal root) to which stimulation is delivered. As another example, IMD 14 may adjust the stimulation by initiating the delivery of stimulation in instances when stimulation is not actively being delivered to the dorsal column and/or dorsal root of patient 12. Conversely, IMD 14 may adjust the stimulation by suspending the delivery of dorsal column stimulation and/or dorsal root stimulation in instances when stimulation is actively being delivered to the dorsal column and the dorsal root of patient 12 in combination with one another.

Such adjustments may be appropriate based on particular activities undertaken by a patient on a daily, weekly, monthly, or general time-related basis. For instance, IMD 14 may automatically adjust the dorsal column and dorsal root stimulation in manner that corresponds with all or a portion of time patient 12 typically sleeps. At such a time, IMD 14 may adjust transition from delivery of stimulation to the dorsal root and dorsal column to only delivery of stimulation to the dorsal column. In other examples, system 10 may include one or more posture state sensors to allow IMD 14 to detect the posture and/or activity of patient 12 and automatically adjust the delivery of dorsal root and dorsal column stimulation based on the detected patient posture and/or activity.

Figure 8:
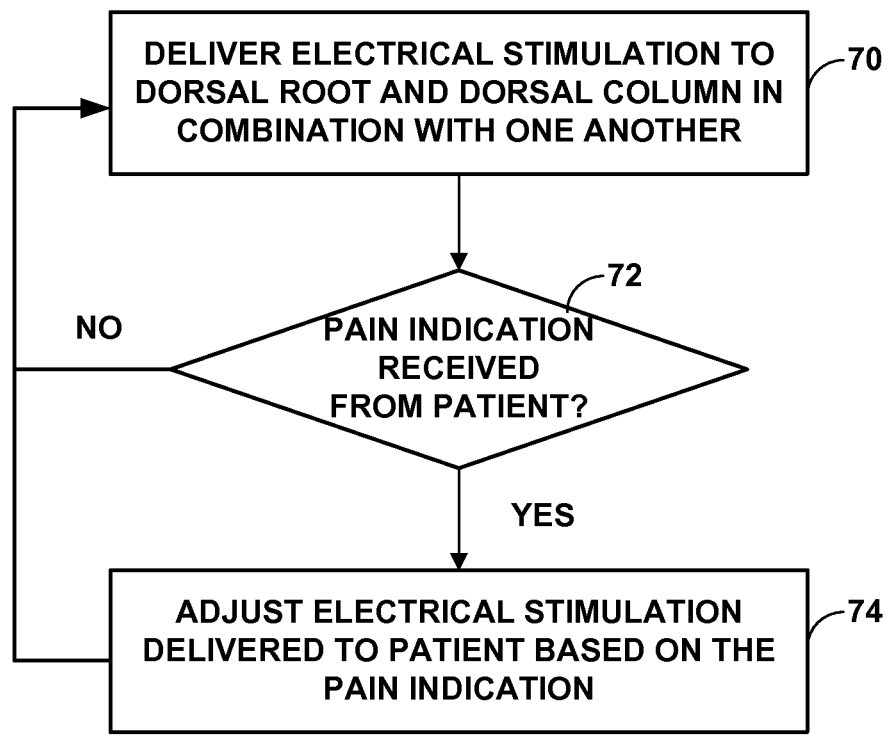
FIG. 8 is a flow diagram illustrating an example technique for adjusting therapy in response to receipt of an indicator indicative of patient pain type.

As another example, IMD 14 may deliver dorsal root and dorsal column therapy based on patient input. FIG. 8 is a flow diagram illustrating an example technique for adjusting such therapy in response to receipt of an indicator indicating patient pain type. As shown in FIG. 8, IMD 14 may deliver dorsal root and dorsal column stimulation to patient 12 in combination with one another, e.g., as described above (70). During the period of time that IMD 14 delivers such therapy to patient 12 (70), processor 28 may receive an indicator indicating that patient 12 is experiencing a generally or specific type of pain (72). For example, patient 12 may indicate the type of pain (e.g., one or more locations that pain is being experienced) to programmer 20, and programmer 20 may communicate the indicated type of pain from patient 12 to IMD 14.

Upon receipt of the indicator, IMD 14 may adjust the electrical stimulation being delivered to patient 12 (74). For example, processor 28 (FIG. 2) may identify a particular combination of dorsal column stimulation and dorsal root stimulation that corresponds to the patient pain type, and adjust the stimulation delivered to the dorsal columns and dorsal roots accordingly. As described above, IMD 14 may adjust the stimulation by initiating, suspending, or adjusting the value of one or more stimulation parameters (e.g., frequency, pulse width, amplitude, electrode configuration) for one or both the dorsal column and dorsal root stimulation. Information identifying particular stimulation program(s) appropriate to treat specific patient pain types may be stored in memory 24. In other examples, processor 38 may identify the particular stimulation corresponding to the patient indicated pain, and communicate the adjustment to IMD 14 via telemetry circuit 40.

As a further illustration, if patient 12 indicates that he/she is experiencing a throbbing pain, IMD 14 may adjust the stimulation to deliver dorsal root stimulation to patient 12. Conversely, if patient 12 indicates that he/she is experiencing a burning pain, IMD 14 may adjust the stimulation to deliver dorsal column stimulation to patient 12. If patient 12 indicates that he/she is experiencing movement-related pain, IMD 14 may adjust the stimulation to deliver both dorsal column and dorsal root stimulation to patient 12, e.g., at substantially the same time. In some examples, IMD 14 may deliver a "burst" of stimulation to a dorsal root (e.g., stimulation over a short amount of time) if patient 12 indicates that he/she is experiencing a specific type of pain. In some cases, one or more programs may be defined for types of pain experienced by patient 12. Such programs may be set-up via programmer 20. Patient pain type may be characterized using one or more suitable techniques. For example, pain indices such as the McGill pain index may be used to characterize patient pain. For each pain characterization, dorsal column and dorsal root stimulation that effectively treats the pain type may be pre-defined to provide for appropriate adjustment of therapy by processor 26 upon receipt of a signal indicating the type of pain experienced by patient 12.

In some examples, rather than indirectly controlling dorsal column and dorsal root stimulation, e.g., based on patient posture state or patient pain indication, patient 12 may directly control the stimulation delivered by IMD 14 via programmer 20. For example, patient 12 may control IMD 14 via programmer 20 to deliver dorsal column stimulation, dorsal root stimulation, or some combination thereof when desired by patient 12.

In some examples, the delivery of dorsal column stimulation and dorsal root stimulation may be controlled by IMD 14 based on progression of a patient condition (e.g., disease progression). In some cases, the particular symptom(s) experienced by patient 12 may change as the patient condition progresses. For example, in the early stages of a disease, patient 12 may experience particular types of pain or pain in areas that are different from that experienced in the middle or later stages of the disease. During the early stages, a first type of dorsal column and dorsal root stimulation may be appropriate, while a different type of therapy may be appropriate during the middle or later stages. As such, IMD 14 may be configured to adjust the dorsal column and dorsal root stimulation based at least in part on such disease progression. Such progression may be tracked on a temporal basis and/or based on patient or clinician feedback indicating the occurrence of particular objective or subjective benchmarks.

Example electrode and lead designs may allow for stimulation of multiple targets including delivery of both dorsal column and dorsal root stimulation. As shown in FIG. 5, IMD 14 may deliver stimulation to both dorsal root and dorsal column stimulation via one more electrodes on trifurcated lead 48. In some examples, a wide paddle lead including suitably configured electrodes may allow for delivery of both dorsal root and dorsal column stimulation from IMD 14. In other examples, individually steerable branching leads/electrodes may be utilized. A lead with segmented electrodes may be used to allow for field steering toward a desired dorsal root and dorsal column location.

Figure 9:
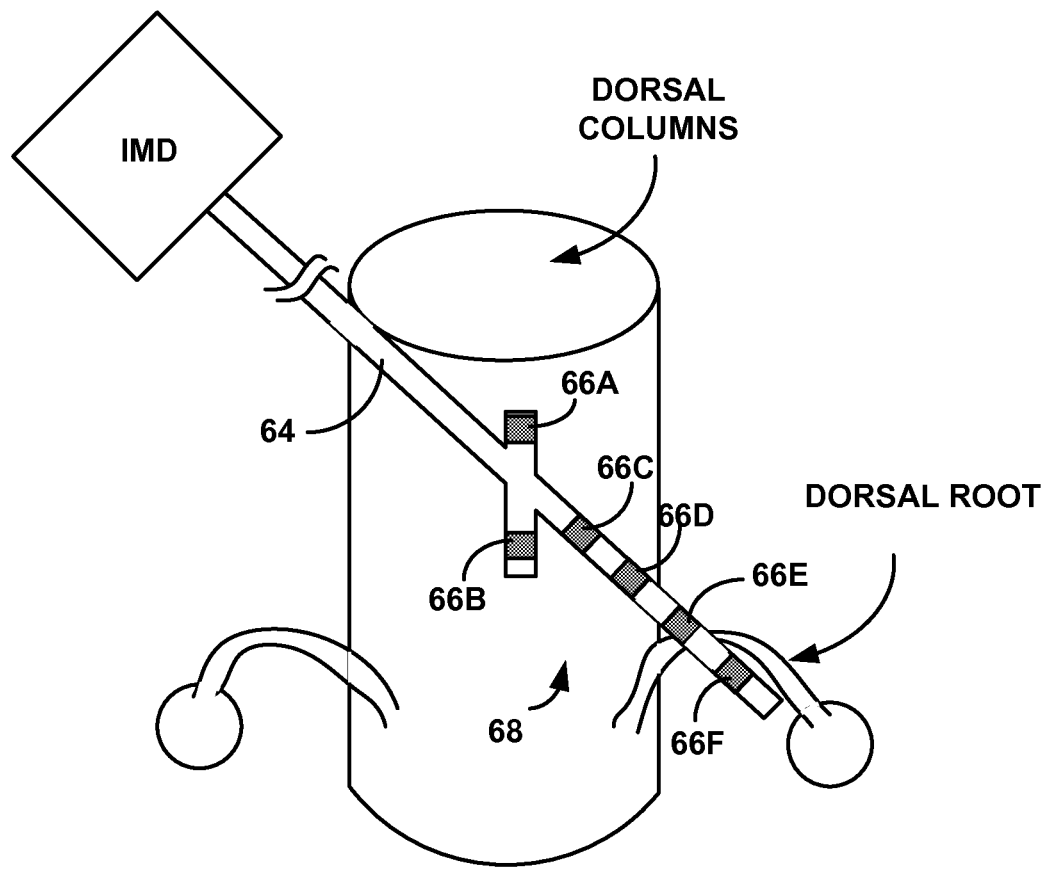
FIG. 9 is a conceptual diagram illustrating an example lead for delivering dorsal column stimulation in combination with dorsal root stimulation.

FIG. 9 is a conceptual illustration of example lead 64 for delivery of both dorsal column and dorsal root stimulation. The distal portion 68 of lead 64 includes electrodes 66A-F. As shown, respective electrodes are positioned adjacent either the dorsal column and/or a dorsal root of a patient when implanted. In some aspects lead 64 may resemble a retrogradely place lead for targeting dorsal roots for stimulation. However, lead 64 includes additional electrodes 66A and 66B that provide a bipole positioned over the dorsal column. In such a configuration, an IMD (e.g., IMD 14) may deliver both dorsal column stimulation and dorsal root stimulation to a patient via lead 64. In other examples, multiple leads may be used to deliver both the dorsal column stimulation and dorsal root stimulation to a patient. As described above, dorsal column stimulation may be delivered in combination with the delivery of dorsal root stimulation, e.g., either substantially simultaneously or interleaved with one another.

While examples of the disclosure are described with regard to delivering stimulation therapy to one or more locations to treat pain experienced by a patient, other types of stimulation therapies are contemplated. For example, dorsal column simulation, dorsal root stimulation and/or PNS may be delivered as therapies to treat one or more other patient conditions, such as, e.g., incontinence, sexual dysfunction, gastrointestinal disorders, and the like.

Furthermore, while examples of the disclosure involving electrical stimulation of one or more peripheral nerves may be described in terms of PNS, stimulation of the one or more peripheral nerves is not limited as such. For example, one or more peripheral nerves may be stimulated to evoked signals at one or more locations in the dorsal columns via peripheral nerve field stimulation (PNFS). PNFS is electrical stimulation delivered via one or more implanted electrodes. The electrodes are positioned, i.e., implanted, in the tissue of a patient within or proximal to the region where the patient experiences pain. The electrodes may be implanted within, for example, intra-dermal, deep dermal, or subcutaneous tissues of the patient. The PNFS current may spread along paths of lower resistance in any of numerous directions from electrodes, but generally spreads parallel to the skin surface. The PNFS current may spread over an area of several centimeters. PNFS is not delivered to a specific nerve, but could be conducted within the innervations territory of a specific defined nerve.

Depending on the location at which the electrodes are implanted PNFS may be used to treat a variety of types of pain. PNFS may be particularly effective at treating localized types of pain. For example, PNFS may be used to treat pain associated with failed back surgery syndrome (FBBS) or other low back pain, cervical pain, such as in the shoulder or neck, neuralgia or other pain associated with occipital nerves, supra-orbital pain, facial pain, inguinal or other pelvic pain, intercostal or other chest pain, limb pains, phantom limb pain, visceral pain, especially if it is referred to a superficial structure, peroneal pain, or arthritis.

PNFS may ameliorate pain within the region through stimulation of axons or nerve fibers in the nearby dermal, subcutaneous, or muscular tissues, or the tissues themselves. In some examples, the stimulation of these axons or fibers may cause, e.g., orthodromic action potentials that propagate toward the spinal cord, and modulate signals from smaller peripheral nerves and dorsal horn cells and/or synapses within the dermatomes that include the pain region, which may reduce pain experienced by a patient in that region. The patient may experience paresthesia in the dermatome where the electrodes are placed. In some examples, the stimulation of these axons or fibers may also cause antidromic action potentials that propagate toward the skin and, e.g., modulate sympathetic outflow, which may reduce pain mediated by the sympathetic system, such as with some forms of complex regional pain syndrome. The electrodes that deliver PNFS are not deliberately implanted proximate to or aligned with larger, peripheral nerves, to avoid delivery of stimulation to smaller fibers in the peripheral nerves, e.g., A-delta fibers, which may result in a patient experiencing unpleasant sensations at some amplitudes.

By way of contrast, peripheral nerve stimulation (PNS) involves delivery of stimulation to a specific peripheral nerve via one or more electrodes implanted proximate to or in contact with a peripheral nerve, e.g., cuff electrodes surrounding the peripheral nerve. PNS may be used to deliver stimulation to, for example, the vagal nerves, cranial nerves, trigeminal nerves, ulnar nerves, median nerves, radial nerves, tibial nerves, and the common peroneal nerves. When PNS is delivered to treat pain, one or more electrodes may be implanted proximate to or in contact with a specific peripheral nerve or branch that is responsible for the pain sensation.

PNS may cause orthodromic and antidromic action potentials to propagate to the spinal cord via the specific peripheral nerve, diminishing pain. In some cases, however, the electrodes for delivering stimulation are implanted proximate to the injured part of the peripheral nerve, are located "upstream" from the region in which a patient perceives the pain, i.e., closer to the spinal cord than the region of pain. For PNS therapy, it may be desirable to implant the electrodes upstream from the region in which a patient perceives pain so that the paresthesia resulting from PNS is as widely distributed as the areas innervated by the peripheral nerve, and covers more of that dermatome.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

If implemented in software, the techniques described in this disclosure may be stored on or transmitted over as one or more instructions or code on a computer-readable medium. Computer-readable media may include non-transitory computer storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Many examples of the disclosure have been described. Various modifications may be made without departing from the scope of the claims. These and other examples are within the scope of the following claims.

The invention claimed is:

1. A method comprising:
   delivering a first stimulation therapy to a dorsal root of a patient via an electrical stimulator; and
   delivering a second stimulation therapy to a location on a dorsal column of the patient via the electrical stimulator in combination with the delivery of the first stimulation therapy to the dorsal root of the patient,
   wherein delivery of the first stimulation therapy to the dorsal root is configured to evoke a signal at the location on the dorsal column where the second stimulation therapy is delivered.

2. The method of claim 1, wherein delivering the second stimulation therapy to a location on a dorsal column of the patient in combination with the first stimulation therapy to the dorsal root of the patient comprises delivering the second stimulation therapy substantially simultaneously with delivery of the first stimulation therapy.

3. The method of claim 1, wherein delivering the second stimulation therapy to a location on a dorsal column of the patient in combination with the first stimulation therapy to the dorsal root of the patient comprises delivering the second stimulation therapy interleaved in time with delivery of the first stimulation therapy.

4. The method of claim 1, further comprising:
   receiving an indicator indicative of patient condition; and
   adjusting at least one of the first and second stimulation therapies delivered to the patient based at least in part on the patient condition.

5. The method of claim 4, wherein the patient condition comprises one or more of pain type or pain location.

6. The method of claim 4, wherein adjusting one or more of the first and second stimulation therapies includes at least one of initiating, suspending, or modifying one or more stimulation parameter values of at least one of the first and second stimulation therapies.

7. The method of claim 1, wherein the first stimulation therapy is delivered via one or more first electrodes, and the second stimulation therapy is delivered via one or more second electrodes.

8. The method of claim 7, wherein at least one electrode from each of the one or more first electrodes and the one or more second electrodes are on a same lead.

9. The method of claim 1, wherein at least one of a frequency, amplitude, and pulse width defined by the first stimulation therapy is different from that defined by the second stimulation therapy.

10. The method of claim 1, wherein the electrical stimulator comprises a first electrical stimulator and a second electrical stimulator separate from the first electrical stimulator, wherein delivering the first stimulation therapy to the dorsal root of the patient via the electrical stimulator comprises delivering a first stimulation therapy to a dorsal root of a patient via the first electrical stimulator, and wherein delivering the second stimulation therapy to the location on the dorsal column of the patient via the electrical stimulator in combination with the delivery of the first stimulation therapy comprises delivering the second stimulation therapy to the location on a dorsal column of the patient via the second electrical stimulator in combination with the delivery of the first stimulation therapy.

11. The method of claim 1, wherein the first therapy is configured to treat a first patient condition and the second therapy is configured to treat a second patient condition different from the first patient condition.

12. A system comprising:
   an electrical stimulator configured to deliver a first stimulation therapy to a dorsal root of a patient and a second stimulation therapy to a location on a dorsal column of the patient; and
   at least one processor configured to control the electrical stimulator to deliver the first stimulation therapy to the dorsal root and the second stimulation therapy to the location on the dorsal column of the patient in combination with one another,
   wherein the delivery of the first stimulation therapy to the dorsal root is configured to evoke a signal at the location on the dorsal column where the second stimulation therapy is delivered.

13. The system of claim 12, wherein the at least one processor controls the electrical stimulator to deliver the first stimulation therapy to the dorsal root substantially simultaneously with delivery of the second stimulation therapy to the location on the dorsal column.

14. The system of claim 12, wherein the at least one processor controls the electrical stimulator to deliver the first stimulation therapy to the dorsal root interleaved in time with delivery of the second stimulation therapy to the location on the dorsal column of the patient.

15. The system of claim 12, wherein the at least one processor is configured to receive an indicator indicating patient condition, and adjust at least one of the first and second stimulation therapies delivered to the patient based at least in part on the patient condition.

16. The system of claim 15, wherein the patient condition comprises one or more of pain type or pain location.

17. The system of claim 15, wherein the at least one processor is configured to adjust one or more of the first and second stimulation therapies by at least one of initiating, suspending, or modifying one or more stimulation parameter values of at least one of the first and second stimulation therapies.

18. The system of claim 12, further comprising a first set of electrodes for delivering the first stimulation therapy and a second set of electrodes for delivering the second stimulation therapy.

19. The system of claim 18, further comprising a lead coupled to the electrical stimulator, wherein at least one electrode from each of the first set and the second set are on the lead.

20. The system of claim 12, wherein at least one of a frequency, amplitude, and pulse width defined by the first stimulation therapy is different from that defined by the second stimulation therapy.

21. The system of claim 12, wherein the electrical stimulator comprises a first electrical stimulator and a second electrical stimulator separate from the first electrical stimulator, wherein the first electrical stimulator is configured to deliver a first stimulation therapy to a dorsal root of a patient, and the second electrical stimulator is configured to deliver the second stimulation therapy to the location on a dorsal column of the patient in combination with the delivery of the first stimulation therapy.

22. The system of claim 12, wherein the first therapy is configured to treat a first patient condition and the second therapy is configured to treat a second patient condition different from the first patient condition.

23. A system comprising:
  means for delivering a first stimulation therapy to a dorsal root of a patient; and
  means for delivering a second stimulation therapy to a location on a dorsal column of the patient in combination with the delivery of the first stimulation therapy to the dorsal root of the patient,
  wherein delivery of the first stimulation therapy to the dorsal root is configured to evoke a signal at the location of the dorsal column where the second stimulation therapy is delivered.

24. The system of claim 23, wherein at least one of a frequency, amplitude, and pulse width defined by the first stimulation therapy is different from that defined by the second stimulation therapy.

25. A non-transitory computer-readable storage medium comprising instructions that cause a processor to:
  control an electrical stimulator to deliver a first stimulation therapy to a first location on a dorsal root of a patient; and
  control the electrical stimulator to deliver a second stimulation therapy to a location on a dorsal column of the patient in combination with the delivery of the first stimulation therapy to the dorsal root of the patient,
  wherein delivery of the first stimulation therapy to the dorsal root is configured to evoke a signal at the location of the dorsal column where the second stimulation therapy is delivered.

26. The non-transitory computer-readable storage medium of claim 25, wherein at least one of a frequency, amplitude, and pulse width defined by the first stimulation therapy is different from that defined by the second stimulation therapy.

* * * * *

UNITED STATES PATENT AND TRADEMARK OFFICE
CERTIFICATE OF CORRECTION

| | | |
|---|---|---|
| PATENT NO. | : 8,676,329 B2 | Page 1 of 1 |
| APPLICATION NO. | : 12/855459 | |
| DATED | : March 18, 2014 | |
| INVENTOR(S) | : Wacnik et al. | |

It is certified that error appears in the above-identified patent and that said Letters Patent is hereby corrected as shown below:

In the Claims

Col. 32, Line 14: "therapy to a first location on a dorsal root of a patient" should read --therapy to a dorsal root of a patient--

Signed and Sealed this
Fourteenth Day of April, 2015

Michelle K. Lee
*Director of the United States Patent and Trademark Office*